(12) United States Patent
Glynn (10) Patent No.: US 8,226,701 B2
(45) Date of Patent: Jul. 24, 2012

(54) STENT AND DELIVERY SYSTEM FOR DEPLOYMENT THEREOF

(75) Inventor: Brian A. Glynn, Santa Rosa, CA (US)

(73) Assignee: Trivascular, Inc., Santa Rosa, CA (US)

(*) Notice: Subject to any disclaimer, the term of this patent is extended or adjusted under 35 U.S.C. 154(b) by 430 days.

(21) Appl. No.: 11/861,756

(22) Filed: Sep. 26, 2007

(65) Prior Publication Data

US 2009/0082842 A1 Mar. 26, 2009

(51) Int. Cl.
*A61F 2/06* (2006.01)
(52) U.S. Cl. .................................................. 623/1.11
(58) Field of Classification Search .................. None
See application file for complete search history.

(56) References Cited

U.S. PATENT DOCUMENTS

| | | |
|---|---|---|
| 3,076,737 A | 2/1963 | Roberts |
| 3,631,854 A | 5/1969 | Fryer et al. |
| 3,540,431 A | 11/1970 | Uddin |
| 3,657,744 A | 4/1972 | Ersek |
| 3,669,586 A | 6/1972 | Kramer |
| 3,814,137 A | 6/1974 | Martinez |
| 3,818,511 A | 6/1974 | Goldberg et al. |
| 3,902,198 A | 9/1975 | Cooper |
| 3,991,767 A | 11/1976 | Miller et al. |
| 4,096,227 A | 6/1978 | Gore |
| 4,110,392 A | 8/1978 | Yamazaki |
| 4,140,126 A | 2/1979 | Choudhury |
| 4,183,102 A | 1/1980 | Guiset |
| 4,187,390 A | 2/1980 | Gore |
| 4,208,745 A | 6/1980 | Okita |
| 4,214,587 A | 7/1980 | Sakura, Jr. |
| 4,229,838 A | 10/1980 | Mano |
| 4,248,924 A | 2/1981 | Okita |
| 4,385,093 A | 5/1983 | Hubis |
| 4,416,028 A | 11/1983 | Eriksson et al. |

(Continued)

FOREIGN PATENT DOCUMENTS

EP 0646365 4/1995
(Continued)

OTHER PUBLICATIONS

The AneuRx® Stent Graft System Treatment for AAA brochure, "An Innovative Modular Approach for the Treatment of Abdominal Aortic Aneurysms (AAA)," Medtronic AVE, Inc. 1999.

(Continued)

*Primary Examiner* — Gary Jackson
*Assistant Examiner* — Christopher Schubert
(74) *Attorney, Agent, or Firm* — Grant Anderson LLP (57) ABSTRACT

A stent, a system for delivering a stent and a method of assembling a stent on a stent delivery shaft. The stent delivery system comprises a delivery shaft and a stent configured to be positioned about the delivery shaft. The stent includes an extension extending circumferentially from a portion of the stent to a free end, thereby defining a shoulder surface. A belt has a first portion fixed relative to the delivery shaft and a second portion positioned circumferentially about at least a portion of the stent to retain the stent in an at least partially constrained configuration. A release wire is configured to releasably engage at least a portion of the belt to retain the belt. The shoulder surface engages at least a portion of the belt to minimize axial movement of the belt during release of the release wire from engagement with the belt.

23 Claims, 5 Drawing Sheets

U.S. PATENT DOCUMENTS

| | | | |
|---|---|---|---|
| 4,434,797 A | 3/1984 | Silander | |
| 4,459,252 A | 7/1984 | MacGregor | |
| 4,474,630 A | 10/1984 | Planck et al. | |
| 4,478,665 A | 10/1984 | Hubis | |
| 4,482,516 A | 11/1984 | Bowman et al. | |
| 4,497,074 A | 2/1985 | Rey et al. | |
| 4,503,569 A | 3/1985 | Dotter | |
| 4,512,338 A | 4/1985 | Balko et al. | |
| 4,550,447 A | 11/1985 | Seiler, Jr. et al. | |
| 4,552,707 A | 11/1985 | How | |
| 4,562,596 A | 1/1986 | Kornberg | |
| 4,577,631 A | 3/1986 | Kreamer | |
| 4,580,568 A | 4/1986 | Gianturco | |
| 4,592,754 A | 6/1986 | Gupte et al. | |
| 4,617,932 A | 10/1986 | Kornberg | |
| 4,647,416 A | 3/1987 | Seiler, Jr. et al. | |
| 4,655,769 A | 4/1987 | Zachariades | |
| 4,655,771 A | 4/1987 | Wallsten | |
| 4,665,906 A | 5/1987 | Jervis | |
| 4,705,517 A | 11/1987 | DiPisa, Jr. | |
| 4,731,073 A | 3/1988 | Robinson | |
| 4,733,665 A | 3/1988 | Palmaz | |
| 4,739,762 A | 4/1988 | Palmaz | |
| 4,740,207 A | 4/1988 | Kreamer | |
| 4,743,480 A | 5/1988 | Campbell et al. | |
| 4,760,102 A | 7/1988 | Moriyama et al. | |
| 4,776,337 A | 10/1988 | Palmaz | |
| 4,787,899 A | 11/1988 | Lazarus | |
| 4,816,028 A | 3/1989 | Kapadia et al. | |
| 4,830,003 A | 5/1989 | Wolff et al. | |
| 4,856,516 A | 8/1989 | Hillstead | |
| 4,871,365 A | 10/1989 | Dumican | |
| 4,877,661 A | 10/1989 | House et al. | |
| 4,902,423 A | 2/1990 | Bacino | |
| 4,932,938 A | 6/1990 | Goldberg et al. | |
| 4,941,870 A | 7/1990 | Okada et al. | |
| 4,955,899 A | 9/1990 | Della et al. | |
| 4,957,669 A | 9/1990 | Primm | |
| 4,985,296 A | 1/1991 | Mortimer, Jr. | |
| 4,994,071 A | 2/1991 | MacGregor | |
| 4,994,077 A | 2/1991 | Dobben | |
| 5,019,090 A | 5/1991 | Pinchuk | |
| 5,041,126 A | 8/1991 | Gianturco | |
| 5,052,998 A | 10/1991 | Zimmon | |
| 5,059,211 A | 10/1991 | Stack et al. | |
| 5,064,435 A | 11/1991 | Porter | |
| 5,098,625 A | 3/1992 | Huang et al. | |
| 5,100,422 A | 3/1992 | Berguer et al. | |
| 5,104,399 A | 4/1992 | Lazarus | |
| 5,104,400 A | 4/1992 | Berguer et al. | |
| 5,104,404 A | 4/1992 | Wolff | |
| 5,108,424 A | 4/1992 | Hoffman, Jr. et al. | |
| 5,110,527 A | 5/1992 | Harada et al. | |
| 5,116,365 A | 5/1992 | Hillstead | |
| 5,122,154 A | 6/1992 | Rhodes | |
| 5,123,917 A | 6/1992 | Lee | |
| 5,133,732 A | 7/1992 | Wiktor | |
| 5,135,536 A | 8/1992 | Hillstead | |
| 5,139,480 A | 8/1992 | Hickle et al. | |
| 5,150,304 A | 9/1992 | Berchem et al. | |
| 5,151,105 A | 9/1992 | Kwan-Gett | |
| 5,152,782 A | 10/1992 | Kowligi et al. | |
| 5,156,620 A | 10/1992 | Pigott | |
| 5,163,955 A | 11/1992 | Love | |
| 5,167,614 A | 12/1992 | Tessmann | |
| 5,171,262 A | 12/1992 | MacGregor | |
| 5,192,310 A | 3/1993 | Herweck et al. | |
| 5,195,984 A | 3/1993 | Schatz | |
| 5,197,976 A | 3/1993 | Herweck et al. | |
| 5,197,978 A | 3/1993 | Hess | |
| 5,201,757 A | 4/1993 | Heyn et al. | |
| 5,202,352 A | 4/1993 | Okada et al. | |
| 5,207,695 A | 5/1993 | Trout, III | |
| 5,217,483 A | 6/1993 | Tower | |
| 5,219,355 A | 6/1993 | Parodi et al. | |
| 5,226,913 A | 7/1993 | Pinchuk | |
| 5,234,456 A | 8/1993 | Silvestrini | |
| 5,250,059 A | 10/1993 | Andreas et al. | |
| 5,275,622 A | 1/1994 | Lazarus et al. | |
| 5,282,823 A | 2/1994 | Schwartz et al. | |
| 5,282,824 A | 2/1994 | Gianturco | |
| 5,282,847 A | 2/1994 | Trescony et al. | |
| 5,290,305 A | 3/1994 | Inoue | |
| 5,292,331 A | 3/1994 | Boneau | |
| 5,304,200 A | 4/1994 | Spaulding | |
| 5,314,472 A | 5/1994 | Fontaine | |
| 5,316,023 A | 5/1994 | Palmaz et al. | |
| 5,320,100 A | 6/1994 | Herweck et al. | |
| 5,321,109 A | 6/1994 | Bosse et al. | |
| 5,330,528 A | 7/1994 | Lazim | |
| 5,334,164 A | 8/1994 | Guy et al. | |
| 5,334,201 A | 8/1994 | Cowan | |
| 5,344,426 A | 9/1994 | Lau et al. | |
| 5,344,444 A | 9/1994 | Glastra | |
| 5,344,451 A | 9/1994 | Dayton | |
| 5,350,398 A | 9/1994 | Pavcnik | |
| 5,354,310 A | 10/1994 | Garnic et al. | |
| 5,354,329 A | 10/1994 | Whalen | |
| 5,360,443 A | 11/1994 | Barone et al. | |
| 5,365,996 A | 11/1994 | Crook | |
| 5,366,504 A | 11/1994 | Andersen et al. | |
| 5,370,682 A | 12/1994 | Schmitt | |
| 5,370,691 A | 12/1994 | Samson | |
| 5,374,473 A | 12/1994 | Knox et al. | |
| 5,382,261 A | 1/1995 | Palmaz | |
| 5,383,892 A | 1/1995 | Cardon et al. | |
| 5,383,928 A | 1/1995 | Scott et al. | |
| 5,387,235 A | 2/1995 | Chuter et al. | |
| 5,389,106 A | 2/1995 | Tower et al. | |
| 5,391,147 A | 2/1995 | Imran et al. | |
| 5,397,345 A | 3/1995 | Lazarus | |
| 5,405,377 A | 4/1995 | Cragg | |
| 5,405,378 A | 4/1995 | Strecker | |
| 5,405,379 A | 4/1995 | Lane | |
| 5,411,550 A | 5/1995 | Herweck et al. | |
| 5,415,634 A | 5/1995 | Glynn et al. | |
| 5,423,851 A | 6/1995 | Samuels | |
| 5,433,909 A | 7/1995 | Martakos et al. | |
| 5,437,900 A | 8/1995 | Kuzowski | |
| 5,441,515 A | 8/1995 | Khosravi et al. | |
| 5,443,458 A | 8/1995 | Eury | |
| 5,443,498 A | 8/1995 | Fontaine | |
| 5,445,646 A | 8/1995 | Euteneuer et al. | |
| 5,447,152 A | 9/1995 | Kohsai et al. | |
| 5,449,373 A | 9/1995 | Pinchasik et al. | |
| 5,456,713 A | 10/1995 | Chuter | |
| 5,464,419 A | 11/1995 | Glastra | |
| 5,464,449 A | 11/1995 | Ryan et al. | |
| 5,466,509 A | 11/1995 | Kowllgi et al. | |
| 5,474,824 A | 12/1995 | Martakos et al. | |
| 5,476,506 A | 12/1995 | Lunn | |
| 5,476,589 A | 12/1995 | Bacino | |
| 5,478,330 A | 12/1995 | Imran et al. | |
| 5,480,423 A | 1/1996 | Ravenscroft et al. | |
| 5,489,295 A | 2/1996 | Piplani et al. | |
| 5,505,887 A | 4/1996 | Zdrahala et al. | |
| 5,507,769 A | 4/1996 | Marin et al. | |
| 5,507,770 A | 4/1996 | Turk | |
| 5,512,360 A | 4/1996 | King | |
| 5,514,154 A | 5/1996 | Lau et al. | |
| 5,522,880 A | 6/1996 | Barone et al. | |
| 5,522,881 A | 6/1996 | Lentz | |
| 5,522,883 A | 6/1996 | Slater et al. | |
| 5,524,633 A | 6/1996 | Heaven et al. | |
| 5,527,353 A | 6/1996 | Schmitt | |
| 5,527,355 A | 6/1996 | Ahn | |
| 5,529,653 A | 6/1996 | Glastra | |
| 5,529,820 A | 6/1996 | Nomi et al. | |
| 5,534,024 A | 7/1996 | Rogers et al. | |
| 5,536,274 A | 7/1996 | Neuss | |
| 5,545,135 A | 8/1996 | Iacob et al. | |
| 5,549,662 A | 8/1996 | Fordenbacher | |
| 5,549,663 A | 8/1996 | Cottone, Jr. | |
| 5,552,100 A | 9/1996 | Shannon et al. | |
| 5,554,180 A | 9/1996 | Turk | |
| 5,554,181 A | 9/1996 | Das | |
| 5,554,183 A | 9/1996 | Nazari | |

| | | |
|---|---|---|
| 5,554,185 A | 9/1996 | Block et al. |
| 5,556,414 A | 9/1996 | Turi |
| 5,556,426 A | 9/1996 | Popadiuk et al. |
| 5,560,986 A | 10/1996 | Mortimer, Jr. |
| 5,562,697 A | 10/1996 | Christiansen |
| 5,562,724 A | 10/1996 | Vorwerk et al. |
| 5,562,726 A | 10/1996 | Chuter |
| 5,562,727 A | 10/1996 | Turk et al. |
| 5,562,728 A | 10/1996 | Lazarus et al. |
| 5,569,295 A | 10/1996 | Lam |
| 5,571,171 A | 11/1996 | Barone et al. |
| 5,571,172 A | 11/1996 | Chin |
| 5,571,173 A | 11/1996 | Parodi |
| 5,575,817 A | 11/1996 | Martin |
| 5,575,818 A | 11/1996 | Pinchuk |
| 5,578,071 A | 11/1996 | Parodi |
| 5,578,072 A | 11/1996 | Barone et al. |
| 5,588,964 A | 12/1996 | Imran et al. |
| 5,591,195 A | 1/1997 | Taheri et al. |
| 5,591,197 A | 1/1997 | Orth et al. |
| 5,591,229 A | 1/1997 | Parodi |
| 5,597,378 A | 1/1997 | Jervis |
| 5,603,721 A | 2/1997 | Lau et al. |
| 5,607,478 A | 3/1997 | Lentz et al. |
| 5,609,624 A | 3/1997 | Kalis |
| 5,609,625 A | 3/1997 | Piplani et al. |
| 5,609,627 A | 3/1997 | Goicoechea et al. |
| 5,609,628 A | 3/1997 | Keranen |
| 5,609,629 A | 3/1997 | Fearnot |
| 5,612,885 A | 3/1997 | Love |
| 5,618,301 A | 4/1997 | Hauenstein et al. |
| 5,620,763 A | 4/1997 | House et al. |
| 5,626,599 A | 5/1997 | Bourne et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,632,772 A | 5/1997 | Alcime et al. |
| 5,632,840 A | 5/1997 | Campbell |
| 5,639,278 A | 6/1997 | Dereume et al. |
| 5,641,373 A | 6/1997 | Shannon et al. |
| 5,645,915 A | 7/1997 | Kranzler et al. |
| 5,649,978 A | 7/1997 | Samson |
| 5,653,745 A | 8/1997 | Trescony et al. |
| 5,653,746 A | 8/1997 | Schmitt |
| 5,656,029 A | 8/1997 | Imran et al. |
| 5,662,675 A | 9/1997 | Stockert et al. |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Bynon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,451 A | 11/1997 | Lenker et al. |
| 5,683,453 A | 11/1997 | Palmaz |
| 5,690,644 A | 11/1997 | Yurek et al. |
| 5,693,083 A | 12/1997 | Baker et al. |
| 5,693,084 A | 12/1997 | Chuter |
| 5,693,087 A | 12/1997 | Parodi |
| 5,693,088 A | 12/1997 | Lazarus |
| 5,697,968 A | 12/1997 | Rogers et al. |
| 5,697,971 A | 12/1997 | Fischell et al. |
| 5,700,285 A | 12/1997 | Myers et al. |
| 5,707,378 A | 1/1998 | Ahn et al. |
| 5,707,388 A | 1/1998 | Lauterjung |
| 5,708,044 A | 1/1998 | Branca |
| 5,709,701 A | 1/1998 | Parodi |
| 5,709,703 A | 1/1998 | Lukie et al. |
| 5,712,315 A | 1/1998 | Dolan |
| 5,713,917 A | 2/1998 | Leonhardt et al. |
| 5,716,393 A | 2/1998 | Lindenberg et al. |
| 5,716,395 A | 2/1998 | Myers et al. |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,725,549 A | 3/1998 | Lam |
| 5,728,131 A | 3/1998 | Frantzen et al. |
| 5,733,303 A | 3/1998 | Israel et al. |
| 5,733,325 A | 3/1998 | Robinson et al. |
| 5,735,892 A | 4/1998 | Myers et al. |
| 5,735,893 A | 4/1998 | Lau et al. |
| 5,735,897 A | 4/1998 | Buirge |
| 5,741,324 A | 4/1998 | Glastra |
| 5,741,325 A | 4/1998 | Chaikof et al. |
| 5,747,128 A | 5/1998 | Campbell et al. |
| 5,749,880 A | 5/1998 | Banas et al. |
| 5,749,894 A | 5/1998 | Engelson |
| 5,749,920 A | 5/1998 | Quiachon et al. |
| 5,749,921 A | 5/1998 | Lenker et al. |
| 5,755,772 A | 5/1998 | Evans et al. |
| 5,755,776 A | 5/1998 | Al-Saadon |
| 5,766,203 A | 6/1998 | Imran et al. |
| 5,769,882 A | 6/1998 | Fogarty et al. |
| 5,769,885 A | 6/1998 | Quiachon et al. |
| 5,769,887 A | 6/1998 | Brown et al. |
| 5,772,884 A | 6/1998 | Tanaka et al. |
| 5,776,142 A | 7/1998 | Gunderson |
| 5,776,161 A | 7/1998 | Globerman |
| 5,776,183 A | 7/1998 | Kanesaka et al. |
| 5,780,807 A | 7/1998 | Saunders |
| 5,782,789 A | 7/1998 | Herweck et al. |
| 5,782,838 A | 7/1998 | Beyar et al. |
| 5,782,904 A | 7/1998 | White et al. |
| 5,782,909 A | 7/1998 | Quiachon et al. |
| 5,785,679 A | 7/1998 | Abolfathi et al. |
| 5,788,626 A | 8/1998 | Thompson |
| 5,789,047 A | 8/1998 | Sasaki et al. |
| 5,797,951 A | 8/1998 | Mueller |
| 5,798,924 A | 8/1998 | Eufinger et al. |
| 5,799,384 A | 9/1998 | Schwartz et al. |
| 5,800,508 A | 9/1998 | Goicoechea et al. |
| 5,800,512 A | 9/1998 | Lentz et al. |
| 5,800,515 A | 9/1998 | Nadal et al. |
| 5,800,518 A | 9/1998 | Piplani et al. |
| 5,800,522 A | 9/1998 | Campbell et al. |
| 5,800,524 A | 9/1998 | Borghi |
| 5,800,526 A | 9/1998 | Anderson et al. |
| 5,810,870 A | 9/1998 | Myers et al. |
| 5,810,872 A | 9/1998 | Kanesaka et al. |
| 5,814,405 A | 9/1998 | Branca et al. |
| 5,817,102 A | 10/1998 | Johnson et al. |
| 5,824,037 A | 10/1998 | Fogarty et al. |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,046 A | 10/1998 | Smith et al. |
| 5,824,058 A | 10/1998 | Ravenscroft et al. |
| 5,827,289 A | 10/1998 | Reiley et al. |
| 5,827,310 A | 10/1998 | Spoeistra |
| 5,827,320 A | 10/1998 | Richter et al. |
| 5,827,321 A | 10/1998 | Roubin et al. |
| 5,833,651 A | 11/1998 | Donovan et al. |
| 5,833,707 A | 11/1998 | McIntyre et al. |
| 5,836,964 A | 11/1998 | Richter et al. |
| 5,836,966 A | 11/1998 | St. Germain |
| 5,840,775 A | 11/1998 | Howard, Jr. et al. |
| 5,843,158 A | 12/1998 | Lenker et al. |
| 5,843,160 A | 12/1998 | Rhodes |
| 5,843,162 A | 12/1998 | Inoue |
| 5,843,164 A | 12/1998 | Frantzen et al. |
| 5,843,166 A | 12/1998 | Lentz et al. |
| 5,843,167 A | 12/1998 | Dwyer et al. |
| 5,843,170 A | 12/1998 | Ahn |
| 5,843,173 A | 12/1998 | Shannon et al. |
| 5,843,175 A | 12/1998 | Frantzen |
| 5,853,419 A | 12/1998 | Imran |
| 5,855,598 A | 1/1999 | Pinchuk |
| 5,858,556 A | 1/1999 | Eckert et al. |
| 5,861,027 A | 1/1999 | Trapp |
| 5,871,536 A | 2/1999 | Lazarus |
| 5,871,537 A | 2/1999 | Holman et al. |

| | | | | | |
|---|---|---|---|---|---|
| 5,871,538 A | 2/1999 | Dereume | 6,059,823 A | 5/2000 | Holman et al. |
| 5,873,906 A | 2/1999 | Lau et al. | 6,060,534 A | 5/2000 | Ronan et al. |
| 5,876,432 A | 3/1999 | Lau et al. | 6,063,114 A | 5/2000 | Nash et al. |
| 5,891,193 A | 4/1999 | Robinson et al. | 6,068,626 A | 5/2000 | Harrington et al. |
| 5,904,713 A | 5/1999 | Leschinsky | 6,070,589 A | 6/2000 | Keith et al. |
| 5,906,619 A | 5/1999 | Olson et al. | 6,074,341 A | 6/2000 | Anderson et al. |
| 5,906,641 A | 5/1999 | Thompson et al. | 6,075,180 A | 6/2000 | Sharber et al. |
| 5,910,168 A | 6/1999 | Myers et al. | 6,077,296 A | 6/2000 | Shokoohi et al. |
| 5,910,277 A | 6/1999 | Ishino et al. | 6,077,297 A | 6/2000 | Robinson et al. |
| 5,911,754 A | 6/1999 | Kanesaka et al. | 6,077,298 A | 6/2000 | Tu et al. |
| 5,916,264 A | 6/1999 | Von Oepen et al. | 6,090,128 A | 7/2000 | Douglas |
| 5,919,204 A | 7/1999 | Lukic et al. | 6,093,203 A | 7/2000 | Uflacker |
| 5,922,020 A | 7/1999 | Klein et al. | 6,096,052 A | 8/2000 | Callister et al. |
| 5,925,061 A | 7/1999 | Ogi et al. | 6,096,070 A | 8/2000 | Ragheb et al. |
| 5,925,075 A | 7/1999 | Myers et al. | 6,098,630 A | 8/2000 | Papazoglou |
| 5,931,865 A | 8/1999 | Silverman et al. | 6,102,918 A | 8/2000 | Kerr |
| 5,935,667 A | 8/1999 | Calcote et al. | 6,102,938 A | 8/2000 | Evans et al. |
| 5,939,198 A | 8/1999 | Howard, Jr. et al. | 6,102,940 A | 8/2000 | Robichon et al. |
| 5,944,750 A | 8/1999 | Tanner et al. | 6,103,172 A | 8/2000 | Newman et al. |
| 5,948,016 A | 9/1999 | Jang | 6,106,548 A | 8/2000 | Roubin et al. |
| 5,954,729 A | 9/1999 | Bachmann et al. | 6,110,198 A | 8/2000 | Fogarty et al. |
| 5,955,016 A | 9/1999 | Goldfarb | 6,113,628 A | 9/2000 | Borghi |
| 5,957,973 A | 9/1999 | Quiachon et al. | 6,117,168 A | 9/2000 | Yang et al. |
| 5,961,545 A | 10/1999 | Lentz et al. | 6,123,722 A | 9/2000 | Fogarty et al. |
| 5,961,546 A | 10/1999 | Robinson et al. | 6,124,523 A | 9/2000 | Banas et al. |
| 5,968,068 A | 10/1999 | Dehdashtian et al. | 6,126,685 A | 10/2000 | Lenker et al. |
| 5,968,090 A | 10/1999 | Ratcliff et al. | 6,129,756 A | 10/2000 | Kugler et al. |
| 5,972,023 A | 10/1999 | Tanner et al. | 6,132,457 A | 10/2000 | Chobotov |
| 5,972,027 A | 10/1999 | Johnson | 6,132,459 A | 10/2000 | Piplani et al. |
| 5,972,441 A | 10/1999 | Campbell et al. | 6,139,572 A | 10/2000 | Campbell et al. |
| 5,976,155 A | 11/1999 | Foreman et al. | 6,142,973 A | 11/2000 | Carleton et al. |
| 5,976,179 A | 11/1999 | Inoue | 6,143,014 A | 11/2000 | Dehdashtian et al. |
| 5,976,192 A | 11/1999 | McIntyre et al. | 6,143,015 A | 11/2000 | Nobles |
| 5,976,650 A | 11/1999 | Campbell et al. | 6,143,016 A | 11/2000 | Bleam et al. |
| 5,980,533 A | 11/1999 | Holman | 6,143,021 A | 11/2000 | Staehle |
| 5,980,570 A | 11/1999 | Simpson | 6,143,022 A | 11/2000 | Shull et al. |
| 5,984,955 A | 11/1999 | Wisselink | 6,146,389 A | 11/2000 | Geitz |
| 5,984,956 A | 11/1999 | Tweden et al. | 6,146,416 A | 11/2000 | Andersen et al. |
| 5,984,964 A | 11/1999 | Roberts et al. | 6,146,417 A | 11/2000 | Ischinger |
| 5,989,287 A | 11/1999 | Yang et al. | 6,149,665 A | 11/2000 | Gabbay |
| 5,993,481 A | 11/1999 | Marcade et al. | 6,149,681 A | 11/2000 | Houser et al. |
| 5,993,489 A | 11/1999 | Lewis et al. | 6,149,682 A | 11/2000 | Frid |
| 5,997,573 A | 12/1999 | Quijano et al. | 6,152,944 A | 11/2000 | Holman et al. |
| 6,001,123 A | 12/1999 | Lau | 6,152,956 A | 11/2000 | Pierce |
| 6,004,346 A | 12/1999 | Wolff et al. | 6,156,063 A | 12/2000 | Douglas |
| 6,004,347 A | 12/1999 | McNamara et al. | 6,156,064 A | 12/2000 | Chouinard |
| 6,004,348 A | 12/1999 | Banas et al. | 6,159,229 A | 12/2000 | Jendersee et al. |
| 6,007,575 A | 12/1999 | Samuels | 6,159,237 A | 12/2000 | Alt et al. |
| 6,015,429 A | 1/2000 | Lau et al. | 6,159,238 A | 12/2000 | Killion et al. |
| 6,015,431 A | 1/2000 | Thornton et al. | 6,159,239 A | 12/2000 | Greenhalgh |
| 6,015,432 A | 1/2000 | Rakos et al. | 6,159,565 A | 12/2000 | Campbell et al. |
| 6,017,362 A | 1/2000 | Lau | 6,162,243 A | 12/2000 | Gray et al. |
| 6,017,364 A | 1/2000 | Lazarus | 6,162,245 A | 12/2000 | Jayaraman |
| 6,019,778 A | 2/2000 | Wilson et al. | 6,162,246 A | 12/2000 | Barone |
| 6,019,779 A | 2/2000 | Thorud et al. | 6,165,210 A | 12/2000 | Lau et al. |
| 6,019,787 A | 2/2000 | Richard et al. | 6,165,211 A | 12/2000 | Thompson |
| 6,022,359 A | 2/2000 | Frantzen | 6,165,212 A | 12/2000 | Dereume et al. |
| 6,024,763 A | 2/2000 | Lenker et al. | 6,165,213 A | 12/2000 | Goicoechea et al. |
| 6,025,044 A | 2/2000 | Campbell et al. | 6,165,214 A | 12/2000 | Lazarus |
| 6,027,779 A | 2/2000 | Campbell et al. | 6,168,610 B1 | 1/2001 | Marin et al. |
| 6,027,811 A | 2/2000 | Campbell et al. | 6,168,614 B1 | 1/2001 | Andersen et al. |
| 6,030,413 A | 2/2000 | Lazarus | 6,168,616 B1 | 1/2001 | Brown, III |
| 6,030,414 A | 2/2000 | Taheri | 6,168,617 B1 | 1/2001 | Blaeser et al. |
| 6,030,415 A | 2/2000 | Chuter | 6,168,618 B1 | 1/2001 | Frantzen |
| 6,036,640 A | 3/2000 | Corace et al. | 6,168,619 B1 | 1/2001 | Dinh et al. |
| 6,036,702 A | 3/2000 | Bachinski et al. | 6,168,620 B1 | 1/2001 | Kerr |
| 6,036,723 A | 3/2000 | Anidjar et al. | 6,174,326 B1 | 1/2001 | Kitaoka et al. |
| 6,036,724 A | 3/2000 | Lentz et al. | 6,183,481 B1 | 2/2001 | Lee et al. |
| 6,036,725 A | 3/2000 | Avellanet | 6,183,504 B1 | 2/2001 | Inoue |
| 6,039,754 A | 3/2000 | Caro | 6,187,034 B1 | 2/2001 | Frantzen |
| 6,039,758 A | 3/2000 | Quiachon et al. | 6,187,036 B1 | 2/2001 | Shaolian et al. |
| 6,042,589 A | 3/2000 | Marianne | 6,187,054 B1 | 2/2001 | Colone et al. |
| 6,042,605 A | 3/2000 | Martin et al. | 6,193,745 B1 | 2/2001 | Fogarty et al. |
| 6,042,606 A | 3/2000 | Frantzen | 6,196,230 B1 | 3/2001 | Hall et al. |
| 6,045,557 A | 4/2000 | White et al. | 6,197,046 B1 | 3/2001 | Piplani et al. |
| 6,048,484 A | 4/2000 | House et al. | 6,197,049 B1 | 3/2001 | Shaolian et al. |
| 6,051,020 A | 4/2000 | Goicoechea et al. | 6,200,339 B1 | 3/2001 | Leschinsky et al. |
| 6,053,943 A | 4/2000 | Edwin et al. | 6,203,550 B1 | 3/2001 | Olson |
| 6,059,821 A | 5/2000 | Anidjar et al. | 6,203,568 B1 | 3/2001 | Lombardi et al. |

| | | |
|---|---|---|
| 6,203,569 B1 | 3/2001 | Wijay |
| 6,203,735 B1 | 3/2001 | Edwin et al. |
| 6,203,779 B1 | 3/2001 | Ricci et al. |
| 6,210,422 B1 | 4/2001 | Douglas |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,039 B1 | 4/2001 | Banas et al. |
| 6,217,608 B1 | 4/2001 | Penn et al. |
| 6,221,102 B1 | 4/2001 | Baker et al. |
| 6,224,609 B1 | 5/2001 | Ressemann et al. |
| 6,231,562 B1 | 5/2001 | Khosravi et al. |
| 6,235,050 B1 | 5/2001 | Quiachon et al. |
| 6,235,051 B1 | 5/2001 | Murphy |
| 6,238,432 B1 | 5/2001 | Parodi |
| 6,240,616 B1 | 6/2001 | Yan |
| 6,241,759 B1 | 6/2001 | Piplani et al. |
| 6,245,097 B1 | 6/2001 | Inoue |
| 6,245,099 B1 | 6/2001 | Edwin et al. |
| 6,245,100 B1 | 6/2001 | Davila et al. |
| 6,245,101 B1 | 6/2001 | Drasler et al. |
| 6,245,102 B1 | 6/2001 | Jayaraman |
| 6,248,116 B1 | 6/2001 | Chevillon et al. |
| 6,251,132 B1 | 6/2001 | Ravenscroft et al. |
| 6,251,136 B1 | 6/2001 | Guruwaiya et al. |
| 6,254,593 B1 | 7/2001 | Wilson |
| 6,254,632 B1 | 7/2001 | Wu et al. |
| 6,258,073 B1 | 7/2001 | Mauch |
| 6,258,114 B1 | 7/2001 | Konya et al. |
| 6,258,116 B1 | 7/2001 | Hojeibane |
| 6,261,316 B1 | 7/2001 | Shaolian et al. |
| 6,261,317 B1 | 7/2001 | Inoue |
| 6,264,662 B1 | 7/2001 | Lauterjung |
| 6,264,684 B1 | 7/2001 | Banas et al. |
| 6,267,783 B1 | 7/2001 | Letendre et al. |
| 6,267,834 B1 | 7/2001 | Shannon et al. |
| 6,270,524 B1 | 8/2001 | Kim |
| 6,270,525 B1 | 8/2001 | Letendre et al. |
| 6,270,707 B1 | 8/2001 | Hori et al. |
| 6,273,909 B1 | 8/2001 | Kugler et al. |
| 6,273,910 B1 | 8/2001 | Limon |
| 6,273,911 B1 | 8/2001 | Cox et al. |
| 6,280,457 B1 | 8/2001 | Wallace et al. |
| 6,280,466 B1 | 8/2001 | Kugler et al. |
| 6,280,467 B1 | 8/2001 | Leonhardt et al. |
| 6,283,991 B1 | 9/2001 | Cox et al. |
| 6,287,315 B1 | 9/2001 | Wijeratne et al. |
| 6,287,329 B1 | 9/2001 | Duerig et al. |
| 6,287,330 B1 | 9/2001 | Johansson et al. |
| 6,287,335 B1 | 9/2001 | Drasler et al. |
| 6,287,336 B1 | 9/2001 | Globerman et al. |
| 6,290,728 B1 | 9/2001 | Phelps et al. |
| 6,293,966 B1 | 9/2001 | Frantzen |
| 6,293,968 B1 | 9/2001 | Taheri |
| 6,293,969 B1 | 9/2001 | Chuter |
| 6,296,661 B1 | 10/2001 | Davila et al. |
| 6,302,891 B1 | 10/2001 | Nadal |
| 6,302,905 B1 | 10/2001 | Goldsteen et al. |
| 6,302,906 B1 | 10/2001 | Goicoechea et al. |
| 6,302,908 B1 | 10/2001 | Parodi |
| 6,303,100 B1 | 10/2001 | Ricci et al. |
| 6,306,141 B1 | 10/2001 | Jervis |
| 6,306,145 B1 | 10/2001 | Leschinsky |
| 6,306,164 B1 | 10/2001 | Kujawski |
| 6,306,165 B1 | 10/2001 | Patnaik et al. |
| 6,312,458 B1 | 11/2001 | Golds |
| 6,312,460 B2 | 11/2001 | Drasler et al. |
| 6,312,462 B1 | 11/2001 | McDermott et al. |
| 6,315,791 B1 | 11/2001 | Gingras et al. |
| 6,319,276 B1 | 11/2001 | Holman et al. |
| 6,319,278 B1 | 11/2001 | Quinn |
| 6,319,279 B1 | 11/2001 | Shannon et al. |
| 6,322,587 B1 | 11/2001 | Quiachon et al. |
| 6,325,819 B1 | 12/2001 | Pavcnik et al. |
| 6,325,823 B1 | 12/2001 | Horzewski et al. |
| 6,325,824 B2 | 12/2001 | Limon |
| 6,325,825 B1 | 12/2001 | Kula et al. |
| 6,328,762 B1 | 12/2001 | Anderson et al. |
| 6,331,186 B1 | 12/2001 | Wang et al. |
| 6,331,188 B1 | 12/2001 | Lau et al. |
| 6,331,190 B1 | 12/2001 | Shokoohi et al. |
| 6,331,191 B1 | 12/2001 | Chobotov |
| 6,334,869 B1 | 1/2002 | Leonhardt et al. |
| 6,336,937 B1 | 1/2002 | Vonesh et al. |
| 6,344,044 B1 | 2/2002 | Fulkerson et al. |
| 6,344,054 B1 | 2/2002 | Parodi |
| 6,344,055 B1 | 2/2002 | Shukov |
| 6,346,118 B1 | 2/2002 | Baker et al. |
| 6,346,119 B1 | 2/2002 | Kuwahara et al. |
| 6,348,065 B1 | 2/2002 | Brown et al. |
| 6,350,277 B1 | 2/2002 | Kocur |
| 6,352,553 B1 | 3/2002 | van der Burg et al. |
| 6,352,561 B1 | 3/2002 | Leopold et al. |
| 6,355,055 B1 | 3/2002 | Waksman et al. |
| 6,355,056 B1 | 3/2002 | Pnheiro |
| 6,355,060 B1 | 3/2002 | Lenker et al. |
| 6,355,063 B1 | 3/2002 | Calcote |
| 6,357,104 B1 | 3/2002 | Myers |
| 6,358,276 B1 | 3/2002 | Edwin et al. |
| 6,358,284 B1 | 3/2002 | Fearnot et al. |
| 6,361,637 B2 | 3/2002 | Martin et al. |
| 6,363,938 B2 | 4/2002 | Saadat |
| 6,364,856 B1 | 4/2002 | Ding et al. |
| 6,364,904 B1 | 4/2002 | Smith |
| 6,368,346 B1 | 4/2002 | Jadhav |
| 6,368,347 B1 | 4/2002 | Maini et al. |
| 6,368,355 B1 | 4/2002 | Uflacker |
| 6,371,979 B1 * | 4/2002 | Beyar et al. .................. 623/1.12 |
| 6,372,136 B1 | 4/2002 | Nakatsuka |
| 6,375,787 B1 | 4/2002 | Lukic |
| 6,379,381 B1 | 4/2002 | Hossainy et al. |
| 6,379,382 B1 | 4/2002 | Yang |
| 6,379,392 B1 | 4/2002 | Walak |
| 6,383,213 B2 | 5/2002 | Wilson et al. |
| 6,383,214 B1 | 5/2002 | Banas et al. |
| 6,387,119 B2 | 5/2002 | Wolf et al. |
| 6,387,124 B1 | 5/2002 | Buscemi et al. |
| 6,391,050 B1 | 5/2002 | Broome |
| 6,391,052 B2 | 5/2002 | Buirge et al. |
| 6,395,019 B2 | 5/2002 | Chobotov |
| 6,395,022 B1 | 5/2002 | Piplani et al. |
| 6,395,208 B1 | 5/2002 | Herweck et al. |
| 6,398,803 B1 | 6/2002 | Layne et al. |
| 6,402,779 B1 | 6/2002 | Colone et al. |
| 6,406,489 B1 | 6/2002 | Richter et al. |
| 6,409,749 B1 | 6/2002 | Maynard |
| 6,409,750 B1 | 6/2002 | Hyodoh et al. |
| 6,409,754 B1 | 6/2002 | Smith et al. |
| 6,409,756 B1 | 6/2002 | Murphy |
| 6,409,757 B1 | 6/2002 | Trout et al. |
| 6,409,761 B1 | 6/2002 | Jang |
| 6,413,269 B1 | 7/2002 | Bui et al. |
| 6,416,535 B1 | 7/2002 | Lazarus |
| 6,416,536 B1 | 7/2002 | Yee |
| 6,416,537 B1 | 7/2002 | Martakos et al. |
| 6,416,538 B1 | 7/2002 | Ley et al. |
| 6,416,539 B1 | 7/2002 | Hassdenteufel |
| 6,416,542 B1 | 7/2002 | Marcade et al. |
| 6,419,701 B1 | 7/2002 | Cook et al. |
| 6,423,084 B1 | 7/2002 | St. Germain |
| 6,423,089 B1 | 7/2002 | Gingras et al. |
| 6,423,090 B1 | 7/2002 | Hancock |
| 6,425,855 B2 | 7/2002 | Tomonto |
| 6,425,898 B1 | 7/2002 | Wilson et al. |
| 6,428,506 B1 | 8/2002 | Simhambhatla et al. |
| 6,428,565 B1 | 8/2002 | Wisselink |
| 6,428,566 B1 | 8/2002 | Holt |
| 6,428,567 B2 | 8/2002 | Wilson et al. |
| 6,428,569 B1 | 8/2002 | Brown |
| 6,428,570 B1 | 8/2002 | Globerman |
| 6,428,571 B1 | 8/2002 | Lentz et al. |
| 6,432,129 B2 | 8/2002 | DiCaprio |
| 6,432,131 B1 | 8/2002 | Ravenscroft |
| 6,432,132 B1 | 8/2002 | Cottone et al. |
| 6,436,104 B2 | 8/2002 | Hoieibane |
| 6,436,133 B1 | 8/2002 | Furst et al. |
| 6,436,134 B2 | 8/2002 | Richter et al. |
| 6,436,135 B1 | 8/2002 | Goldfarb |

| | | |
|---|---|---|
| 6,440,165 B1 | 8/2002 | Richter et al. |
| 6,443,941 B1 | 9/2002 | Slepian et al. |
| 6,443,979 B1 | 9/2002 | Stalker et al. |
| 6,443,981 B1 | 9/2002 | Colone et al. |
| 6,447,501 B1 | 9/2002 | Solar et al. |
| 6,447,522 B2 | 9/2002 | Gambale et al. |
| 6,451,047 B2 | 9/2002 | McCrea et al. |
| 6,451,050 B1 | 9/2002 | Rudakov et al. |
| 6,451,051 B2 | 9/2002 | Drasler et al. |
| 6,451,053 B1 | 9/2002 | Dehdashtian et al. |
| 6,454,796 B1 | 9/2002 | Barkman et al. |
| 6,461,381 B2 | 10/2002 | Israel et al. |
| 6,464,720 B2 | 10/2002 | Boatman et al. |
| 6,464,721 B1 | 10/2002 | Marcade et al. |
| 6,464,722 B2 | 10/2002 | Israel et al. |
| 6,471,718 B1 | 10/2002 | Staehle et al. |
| 6,471,720 B1 | 10/2002 | Ehr et al. |
| 6,471,721 B1 | 10/2002 | Dang |
| 6,471,722 B1 | 10/2002 | Inoue |
| 6,475,166 B1 | 11/2002 | Escano |
| 6,475,208 B2 | 11/2002 | Mauch |
| 6,475,236 B1 | 11/2002 | Roubin et al. |
| 6,475,237 B2 | 11/2002 | Drasler |
| 6,475,238 B1 | 11/2002 | Fedida |
| 6,475,466 B1 | 11/2002 | Ricci et al. |
| 6,478,807 B1 | 11/2002 | Foreman et al. |
| 6,478,815 B1 | 11/2002 | Alt |
| 6,478,816 B1 | 11/2002 | Kveen et al. |
| 6,482,227 B1 | 11/2002 | Solovay |
| 6,485,507 B1 | 11/2002 | Walak et al. |
| 6,485,508 B1 | 11/2002 | McGuinness |
| 6,485,509 B2 | 11/2002 | Killion et al. |
| 6,485,511 B2 | 11/2002 | Lau et al. |
| 6,485,513 B1 | 11/2002 | Fan |
| 6,485,515 B2 | 11/2002 | Strecker |
| 6,485,524 B2 | 11/2002 | Strecker |
| 6,488,694 B1 | 12/2002 | Lau et al. |
| 6,488,700 B2 | 12/2002 | Klumb et al. |
| 6,488,701 B1 | 12/2002 | Nolting et al. |
| 6,488,705 B2 | 12/2002 | Schmitt et al. |
| 6,491,718 B1 | 12/2002 | Ahmad |
| 6,491,719 B1 | 12/2002 | Fogarty et al. |
| 6,494,875 B1 | 12/2002 | Mauch |
| 6,494,904 B1 | 12/2002 | Love |
| 6,494,907 B1 | 12/2002 | Bulver |
| 6,494,909 B2 | 12/2002 | Greenhalgh |
| 6,497,722 B1 | 12/2002 | Von Oepen et al. |
| 6,497,723 B1 | 12/2002 | Starck et al. |
| 6,500,202 B1 | 12/2002 | Shaolian et al. |
| 6,500,203 B1 | 12/2002 | Thompson et al. |
| 6,500,204 B1 | 12/2002 | Igaki |
| 6,500,532 B1 | 12/2002 | Ruefer et al. |
| 6,503,271 B2 | 1/2003 | Duerig et al. |
| 6,506,211 B1 | 1/2003 | Doran et al. |
| 6,508,833 B2 | 1/2003 | Pavcnik et al. |
| 6,508,834 B1 | 1/2003 | Pinchasik et al. |
| 6,514,281 B1 | 2/2003 | Blaeser et al. |
| 6,517,558 B2 | 2/2003 | Gittings et al. |
| 6,517,571 B1 | 2/2003 | Brauker et al. |
| 6,517,573 B1 | 2/2003 | Pollock et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,520,986 B2 | 2/2003 | Martin et al. |
| 6,524,334 B1 | 2/2003 | Thompson |
| 6,524,335 B1 | 2/2003 | Hartley et al. |
| 6,524,336 B1 | 2/2003 | Papazolgou et al. |
| 6,530,765 B1 | 3/2003 | Zdrahala et al. |
| 6,530,947 B1 | 3/2003 | Euteneuer et al. |
| 6,530,950 B1 | 3/2003 | Alvarado et al. |
| 6,533,806 B1 | 3/2003 | Sullivan et al. |
| 6,533,807 B2 | 3/2003 | Wolinsky et al. |
| 6,533,808 B1 | 3/2003 | Thompson et al. |
| 6,533,811 B1 | 3/2003 | Ryan et al. |
| 6,537,202 B1 | 3/2003 | Frantzen |
| 6,540,778 B1 | 4/2003 | Quiachin et al. |
| 6,540,780 B1 | 4/2003 | Zilla et al. |
| 6,547,813 B2 | 4/2003 | Stiger et al. |
| 6,547,814 B2 | 4/2003 | Edwin et al. |
| 6,547,815 B2 | 4/2003 | Myers |
| 6,547,817 B1 | 4/2003 | Fischell et al. |
| 6,548,013 B2 | 4/2003 | Kadavy et al. |
| 6,551,350 B1 | 4/2003 | Thornton et al. |
| 6,554,857 B1 | 4/2003 | Zilla et al. |
| 6,554,858 B2 | 4/2003 | Dereume et al. |
| 6,558,414 B2 | 5/2003 | Layne |
| 6,558,415 B2 | 5/2003 | Thompson |
| 6,562,063 B1 | 5/2003 | Euteneuer et al. |
| 6,565,597 B1 | 5/2003 | Fearnot |
| 6,569,150 B2 | 5/2003 | Teague |
| 6,569,190 B2 | 5/2003 | Whalen, II et al. |
| 6,569,193 B1 | 5/2003 | Cox et al. |
| 6,572,649 B2 | 6/2003 | Berry et al. |
| 6,575,994 B1 | 6/2003 | Marin |
| 6,576,009 B2 | 6/2003 | Ryan et al. |
| 6,579,314 B1 | 6/2003 | Lombardi et al. |
| 6,582,458 B1 | 6/2003 | White et al. |
| 6,589,274 B2 | 7/2003 | Stiger et al. |
| 6,589,275 B1 | 7/2003 | Ivancev et al. |
| 6,592,614 B2 | 7/2003 | Lenker et al. |
| 6,602,269 B2 | 8/2003 | Wallace et al. |
| 6,602,280 B2 | 8/2003 | Chobotov |
| 6,602,283 B2 | 8/2003 | Doran et al. |
| 6,605,110 B2 | 8/2003 | Harrison |
| 6,607,551 B1 | 8/2003 | Sullivan et al. |
| 6,613,082 B2 | 9/2003 | Yang |
| 6,613,083 B2 | 9/2003 | Alt |
| 6,613,084 B2 | 9/2003 | Yang |
| 6,620,190 B2 | 9/2003 | Colone |
| 6,626,938 B1 | 9/2003 | Butaric et al. |
| 6,635,079 B2 | 10/2003 | Unsworth et al. |
| 6,645,240 B2 | 11/2003 | Yee |
| 6,652,554 B1 | 11/2003 | Wholey et al. |
| 6,652,570 B2 | 11/2003 | Smith et al. |
| 6,652,573 B2 | 11/2003 | von Oepen |
| 6,652,575 B2 | 11/2003 | Wang |
| 6,652,580 B1 | 11/2003 | Chuter |
| 6,656,215 B1 | 12/2003 | Yanez et al. |
| 6,656,506 B1 | 12/2003 | Wu et al. |
| 6,660,030 B2 | 12/2003 | Shaolian et al. |
| 6,663,662 B2 | 12/2003 | Pacetti et al. |
| 6,663,663 B2 | 12/2003 | Kim et al. |
| 6,663,664 B1 | 12/2003 | Pacetti |
| 6,663,665 B2 | 12/2003 | Shaolian et al. |
| 6,663,667 B2 | 12/2003 | Dehdashtian et al. |
| 6,669,720 B1 | 12/2003 | Pierce |
| 6,669,723 B2 | 12/2003 | Killion et al. |
| 6,669,724 B2 | 12/2003 | Park et al. |
| 6,673,102 B1 | 1/2004 | Vonesh et al. |
| 6,673,103 B1 | 1/2004 | Golds et al. |
| 6,673,106 B2 | 1/2004 | Mitelberg et al. |
| 6,673,107 B1 | 1/2004 | Brandt et al. |
| 6,676,667 B2 | 1/2004 | Mareiro et al. |
| 6,676,695 B2 | 1/2004 | Solem |
| 6,679,911 B2 | 1/2004 | Burgermeister |
| 6,685,736 B1 | 2/2004 | White et al. |
| 6,689,158 B1 | 2/2004 | White et al. |
| 6,689,159 B2 | 2/2004 | Hartigan et al. |
| 6,692,523 B2 | 2/2004 | Holman et al. |
| 6,694,983 B2 | 2/2004 | Hall et al. |
| 6,695,833 B1 | 2/2004 | Frantzen |
| 6,695,875 B2 | 2/2004 | Stelter et al. |
| 6,695,877 B2 | 2/2004 | Brucker et al. |
| 6,696,666 B2 | 2/2004 | Merdan et al. |
| 6,699,274 B2 | 3/2004 | Stinson |
| 6,699,277 B1 | 3/2004 | Freidberg et al. |
| 6,702,847 B2 | 3/2004 | DiCarlo |
| 6,702,849 B1 | 3/2004 | Dutta et al. |
| 6,706,064 B1 | 3/2004 | Anson |
| 6,709,449 B2 | 3/2004 | Camrud et al. |
| 6,709,455 B1 | 3/2004 | Chouinard |
| 6,712,827 B2 | 3/2004 | Ellis et al. |
| 6,716,238 B2 | 4/2004 | Elliott |
| 6,716,239 B2 | 4/2004 | Sowinski |
| 6,719,783 B2 | 4/2004 | Lentz et al. |
| 6,726,712 B1 | 4/2004 | Raeder-Devens |
| 6,730,119 B1 | 5/2004 | Smalling |
| 6,733,521 B2 | 5/2004 | Chobotov et al. |

| | | |
|---|---|---|
| 6,736,839 B2 | 5/2004 | Cummings |
| 6,740,111 B1 | 5/2004 | Lauterjung |
| 6,740,114 B2 | 5/2004 | Burgermeister |
| 6,740,115 B2 | 5/2004 | Lombardi |
| 6,743,210 B2 | 6/2004 | Hart et al. |
| 6,743,511 B2 | 6/2004 | Dittrich et al. |
| 6,746,890 B2 | 6/2004 | Gupta |
| 6,752,829 B2 | 6/2004 | Kocur et al. |
| 6,755,855 B2 | 6/2004 | Yurek et al. |
| 6,758,858 B2 | 7/2004 | McCrea et al. |
| 6,761,733 B2 | 7/2004 | Chobotov et al. |
| 6,770,086 B1 | 8/2004 | Girton et al. |
| 6,770,087 B2 | 8/2004 | Layne et al. |
| 6,773,453 B2 | 8/2004 | Ravenscroft |
| 6,773,457 B2 | 8/2004 | Gellman et al. |
| 6,776,604 B1 | 8/2004 | Chobotov et al. |
| 6,776,793 B2 | 8/2004 | Brown et al. |
| 6,786,920 B2 | 9/2004 | Shannon et al. |
| 6,790,227 B2 | 9/2004 | Burgermeister |
| 6,790,230 B2 | 9/2004 | Beyersdorf et al. |
| 6,793,672 B2 | 9/2004 | Khosravi et al. |
| 6,796,999 B2 | 9/2004 | Pinchasik |
| 6,802,849 B2 | 10/2004 | Blaeser et al. |
| 6,802,856 B2 | 10/2004 | Wilson |
| 6,814,753 B2 | 11/2004 | Schmitt |
| 6,818,013 B2 | 11/2004 | Mitelberg et al. |
| 6,821,292 B2 | 11/2004 | Pazienza et al. |
| 6,824,558 B2 | 11/2004 | Parodi |
| 6,827,726 B2 | 12/2004 | Parodi |
| 6,827,731 B2 | 12/2004 | Armstrong et al. |
| 6,827,735 B2 | 12/2004 | Greenberg |
| 6,827,737 B2 | 12/2004 | Hill et al. |
| 6,833,004 B2 | 12/2004 | Ishii et al. |
| 6,841,213 B2 | 1/2005 | Parsonage et al. |
| 6,843,802 B1 | 1/2005 | Villalobos et al. |
| 6,849,086 B2 | 2/2005 | Cragg |
| 6,858,035 B2 | 2/2005 | Whayne |
| 6,860,900 B2 | 3/2005 | Clerc et al. |
| 6,863,685 B2 | 3/2005 | Davila et al. |
| 6,869,443 B2 | 3/2005 | Buscemi et al. |
| 6,878,160 B2 | 4/2005 | Gilligan et al. |
| 6,878,161 B2 | 4/2005 | Lenker |
| 6,884,260 B2 | 4/2005 | Kugler et al. |
| 6,899,728 B1 | 5/2005 | Phillips et al. |
| 6,918,925 B2 | 7/2005 | Tehrani |
| 6,918,927 B2 | 7/2005 | Bates et al. |
| 6,923,827 B2 | 8/2005 | Campbell et al. |
| 6,926,732 B2 | 8/2005 | Derus et al. |
| 6,929,659 B2 | 8/2005 | Pinchuk |
| 6,929,709 B2 | 8/2005 | Smith |
| 6,939,370 B2 | 9/2005 | Hartley et al. |
| 6,939,374 B2 | 9/2005 | Banik et al. |
| 6,942,689 B2 | 9/2005 | Majercak |
| 6,945,989 B1 | 9/2005 | Rourke et al. |
| 6,945,992 B2 | 9/2005 | Goodson et al. |
| 6,949,120 B2 | 9/2005 | Kveen et al. |
| 6,962,602 B2 | 11/2005 | Vardi et al. |
| 6,962,603 B1 | 11/2005 | Brown |
| 6,964,677 B2 | 11/2005 | Osypka |
| 6,974,471 B2 | 12/2005 | Van Schie et al. |
| 6,974,472 B2 | 12/2005 | Hong et al. |
| 6,981,982 B2 | 1/2006 | Armstrong et al. |
| 6,989,026 B2 | 1/2006 | Richter et al. |
| 6,994,722 B2 | 2/2006 | DiCarlo |
| 6,997,945 B2 | 2/2006 | Germain |
| 6,998,060 B2 | 2/2006 | Tomonto |
| 7,001,407 B2 | 2/2006 | Hansen et al. |
| 7,001,419 B2 | 2/2006 | DiCaprio et al. |
| 7,001,431 B2 | 2/2006 | Bao et al. |
| 7,011,673 B2 | 3/2006 | Fischell et al. |
| 7,011,674 B2 | 3/2006 | Brenneman |
| 7,022,132 B2 | 4/2006 | Kocur |
| 7,022,135 B2 | 4/2006 | Zilla et al. |
| 7,033,389 B2 | 4/2006 | Sherry |
| 7,056,325 B1 | 6/2006 | Makower |
| 7,056,336 B2 | 6/2006 | Armstrong et al. |
| 7,056,412 B2 | 6/2006 | Henderson |
| 7,066,951 B2 | 6/2006 | Chobotov |
| 7,073,504 B2 | 7/2006 | Callister et al. |
| 7,081,129 B2 | 7/2006 | Chobotov |
| 7,081,132 B2 | 7/2006 | Cook |
| 7,083,642 B2 | 8/2006 | Sirhan et al. |
| 7,090,693 B1 | 8/2006 | Chobotov et al. |
| 7,094,255 B2 | 8/2006 | Penn et al. |
| 7,108,715 B2 | 9/2006 | Lawrence-Brown et al. |
| 7,115,140 B2 | 10/2006 | Stoltze et al. |
| 7,125,464 B2 | 10/2006 | Chobotov et al. |
| 7,128,754 B2 | 10/2006 | Bolduc |
| 7,128,755 B2 | 10/2006 | Su et al. |
| 7,147,455 B2 | 12/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,160,318 B2 | 1/2007 | Greenberg et al. |
| 7,166,125 B1 | 1/2007 | Baker et al. |
| 7,175,651 B2 | 2/2007 | Kerr |
| 7,175,652 B2 | 2/2007 | Cook et al. |
| 7,189,256 B2 | 3/2007 | Smith |
| 7,192,441 B2 | 3/2007 | Sherry |
| 7,223,280 B2 | 5/2007 | Anson et al. |
| 7,226,474 B2 | 6/2007 | Iancea et al. |
| 7,229,470 B2 | 6/2007 | Brown et al. |
| 7,232,459 B2 | 6/2007 | Greenberg |
| 7,244,242 B2 | 7/2007 | Freyman |
| 7,273,494 B2 | 9/2007 | Rolando et al. |
| 7,284,399 B1 | 10/2007 | Sisco |
| 7,294,147 B2 | 11/2007 | Hartley |
| 7,314,484 B2 | 1/2008 | Deem et al. |
| 7,338,518 B2 | 3/2008 | Chobotov |
| 7,351,256 B2 | 4/2008 | Hojeibane et al. |
| 7,425,219 B2 | 9/2008 | Quadri |
| 7,452,374 B2 | 11/2008 | Hain et al. |
| 7,465,270 B2 | 12/2008 | Li |
| 7,485,138 B2 | 2/2009 | Fearnot et al. |
| 7,491,230 B2 | 2/2009 | Holman et al. |
| 7,491,234 B2 | 2/2009 | Palasis et al. |
| 7,500,988 B1 | 3/2009 | Butaric et al. |
| 7,510,571 B2 | 3/2009 | Spiridigliozzi et al. |
| 7,520,890 B2 | 4/2009 | Phillips |
| 7,520,895 B2 | 4/2009 | Douglas et al. |
| 7,530,988 B2 | 5/2009 | Evans et al. |
| 7,550,004 B2 | 6/2009 | Bahler et al. |
| 7,550,005 B2 | 6/2009 | Bates et al. |
| 7,556,645 B2 | 7/2009 | Lashinski et al. |
| 7,591,843 B1 | 9/2009 | Escano |
| 7,597,710 B2 | 10/2009 | Obermiller |
| 8,066,755 B2 | 11/2011 | Zacharias et al. |
| 2001/0014794 A1 | 8/2001 | Moll |
| 2001/0029349 A1 | 10/2001 | Leschinsky |
| 2001/0039445 A1 | 11/2001 | Hall et al. |
| 2001/0041928 A1 | 11/2001 | Pavcnik et al. |
| 2001/0044652 A1 | 11/2001 | Moore |
| 2001/0049534 A1 | 12/2001 | Lachat |
| 2002/0007193 A1 | 1/2002 | Tanner et al. |
| 2002/0011684 A1 | 1/2002 | Bahar et al. |
| 2002/0016626 A1 | 2/2002 | DiMatteo et al. |
| 2002/0019659 A1 | 2/2002 | Goicoechea et al. |
| 2002/0029051 A1 | 3/2002 | Callister et al. |
| 2002/0032408 A1 | 3/2002 | Parker et al. |
| 2002/0035395 A1 | 3/2002 | Sugimoto |
| 2002/0040236 A1 | 4/2002 | Lau et al. |
| 2002/0040237 A1 | 4/2002 | Lentz et al. |
| 2002/0042644 A1 | 4/2002 | Greenhalgh |
| 2002/0045931 A1 | 4/2002 | Sogard et al. |
| 2002/0045933 A1 | 4/2002 | Jang |
| 2002/0045934 A1 | 4/2002 | Jang |
| 2002/0045935 A1 | 4/2002 | Jang |
| 2002/0049487 A1 | 4/2002 | Lootz et al. |
| 2002/0049490 A1 | 4/2002 | Pollock et al. |
| 2002/0049493 A1 | 4/2002 | Jang |
| 2002/0052627 A1 | 5/2002 | Boylan et al. |
| 2002/0052644 A1 | 5/2002 | Shaolian et al. |
| 2002/0052649 A1 | 5/2002 | Greenhalgh |
| 2002/0055768 A1 | 5/2002 | Hess et al. |
| 2002/0065552 A1 | 5/2002 | Jayaraman et al. |
| 2002/0072792 A1 | 6/2002 | Burgermeister et al. |
| 2002/0072793 A1 | 6/2002 | Rolando et al. |
| 2002/0076542 A1 | 6/2002 | Kramer et al. |

| | | | | | | |
|---|---|---|---|---|---|---|
| 2002/0077692 A1 | 6/2002 | Besselink | | 2005/0228484 A1 | 10/2005 | Stephens et al. |
| 2002/0082680 A1 | 6/2002 | Shanley et al. | | 2006/0009833 A1 | 1/2006 | Chobotov et al. |
| 2002/0082682 A1 | 6/2002 | Barclay et al. | | 2006/0020319 A1 | 1/2006 | Kim |
| 2002/0082685 A1 | 6/2002 | Sirhan et al. | | 2006/0079952 A1 | 4/2006 | Kaplan et al. |
| 2002/0095208 A1 | 7/2002 | Gregorich et al. | | 2006/0136047 A1 | 6/2006 | Obermiller et al. |
| 2002/0096252 A1 | 7/2002 | Lukic | | 2006/0149364 A1 | 7/2006 | Walak et al. |
| 2002/0107561 A1 | 8/2002 | Pinheiro | | 2006/0178732 A1* | 8/2006 | Chobotov et al. ............ 623/1.34 |
| 2002/0120321 A1 | 8/2002 | Gunderson et al. | | 2006/0186143 A1 | 8/2006 | Argentine |
| 2002/0120327 A1 | 8/2002 | Cox et al. | | 2006/0212112 A1 | 9/2006 | Evans et al. |
| 2002/0123790 A1 | 9/2002 | White et al. | | 2006/0224232 A1 | 10/2006 | Chobotov |
| 2002/0123791 A1 | 9/2002 | Harrison | | 2006/0233990 A1 | 10/2006 | Humphrey et al. |
| 2002/0123796 A1 | 9/2002 | Majercak et al. | | 2006/0233991 A1 | 10/2006 | Humphrey et al. |
| 2002/0143387 A1 | 10/2002 | Soetikno et al. | | 2006/0287713 A1 | 12/2006 | Douglas et al. |
| 2002/0147492 A1 | 10/2002 | Shokoohi et al. | | 2006/0292206 A1 | 12/2006 | Kim et al. |
| 2002/0151953 A1* | 10/2002 | Chobotov et al. ............ 623/1.11 | | 2007/0012396 A1 | 1/2007 | Chobotov et al. |
| 2002/0151956 A1 | 10/2002 | Chobotov et al. | | 2007/0016281 A1 | 1/2007 | Melsheimer |
| 2002/0161376 A1 | 10/2002 | Barry et al. | | 2007/0055347 A1 | 3/2007 | Arbefeuille |
| 2002/0165603 A1 | 11/2002 | Thornton et al. | | 2007/0112413 A1 | 5/2007 | Smith |
| 2002/0169497 A1 | 11/2002 | Wholey et al. | | 2007/0162106 A1 | 7/2007 | Evans et al. |
| 2002/0183826 A1 | 12/2002 | Dorn et al. | | 2007/0167901 A1 | 7/2007 | Herrig et al. |
| 2002/0183827 A1 | 12/2002 | Derus et al. | | 2007/0203571 A1 | 8/2007 | Kaplan et al. |
| 2002/0188346 A1 | 12/2002 | Healy et al. | | 2007/0219627 A1 | 9/2007 | Chu et al. |
| 2002/0188347 A1 | 12/2002 | Mathis | | 2007/0239273 A1 | 10/2007 | Allen |
| 2002/0193867 A1 | 12/2002 | Gladdish, Jr. et al. | | 2007/0244539 A1 | 10/2007 | Lentz et al. |
| 2002/0193872 A1 | 12/2002 | Trout et al. | | 2007/0276477 A1 | 11/2007 | Lee et al. |
| 2002/0193873 A1 | 12/2002 | Brucker et al. | | 2007/0282369 A1 | 12/2007 | Gilson et al. |
| 2002/0198585 A1 | 12/2002 | Wisselink | | 2008/0015687 A1 | 1/2008 | Lashinski et al. |
| 2002/0198587 A1 | 12/2002 | Greenberg et al. | | 2008/0027529 A1 | 1/2008 | Hartley et al. |
| 2003/0004560 A1 | 1/2003 | Chobotov et al. | | 2008/0051705 A1 | 2/2008 | Von Oepen et al. |
| 2003/0004565 A1 | 1/2003 | Harnek et al. | | 2008/0114441 A1 | 5/2008 | Rust |
| 2003/0009212 A1 | 1/2003 | Kerr | | 2008/0114442 A1 | 5/2008 | Mitchell et al. |
| 2003/0014075 A1 | 1/2003 | Rosenbluth et al. | | 2008/0114443 A1 | 5/2008 | Mitchell |
| 2003/0040803 A1 | 2/2003 | Rioux et al. | | 2008/0172119 A1 | 7/2008 | Yamasaki et al. |
| 2003/0050684 A1 | 3/2003 | Abrams et al. | | 2008/0228255 A1 | 9/2008 | Rust |
| 2003/0068296 A1 | 4/2003 | Ricci et al. | | 2008/0234800 A1 | 9/2008 | Clarke |
| 2003/0083736 A1 | 5/2003 | Brown et al. | | 2009/0036971 A1 | 2/2009 | Humphrey et al. |
| 2003/0097170 A1 | 5/2003 | Friedrich et al. | | 2009/0042796 A1 | 2/2009 | Wallach et al. |
| 2003/0120263 A1 | 6/2003 | Ouriel et al. | | 2009/0082841 A1 | 3/2009 | Zacharias et al. |
| 2003/0120331 A1 | 6/2003 | Chobotov et al. | | 2009/0082842 A1 | 3/2009 | Glynn |
| 2003/0125797 A1 | 7/2003 | Chobotov | | 2009/0082844 A1 | 3/2009 | Zacharias et al. |
| 2003/0135256 A1 | 7/2003 | Gallagher et al. | | 2009/0082845 A1 | 3/2009 | Chobotov et al. |
| 2003/0135261 A1 | 7/2003 | Kugler et al. | | 2009/0082846 A1 | 3/2009 | Chobotov et al. |
| 2003/0176912 A1 | 9/2003 | Chuter et al. | | 2009/0082847 A1 | 3/2009 | Zacharias et al. |
| 2003/0191518 A1 | 10/2003 | Spiridigliozzi et al. | | 2009/0099649 A1 | 4/2009 | Chobotov et al. |
| 2003/0204236 A1 | 10/2003 | Letort | | 2009/0132020 A1 | 5/2009 | Watson |
| 2003/0204244 A1 | 10/2003 | Stiger | | 2009/0132026 A1 | 5/2009 | Martin et al. |
| 2003/0212449 A1 | 11/2003 | Cox | | 2009/0171431 A1 | 7/2009 | Swanson et al. |
| 2003/0220683 A1 | 11/2003 | Minasian | | 2009/0182406 A1 | 7/2009 | Eidenschink |
| 2003/0225453 A1 | 12/2003 | Murch | | 2009/0198267 A1 | 8/2009 | Evans et al. |
| 2004/0024446 A1 | 2/2004 | Smith | | 2009/0287145 A1 | 11/2009 | Cragg |
| 2004/0034407 A1 | 2/2004 | Sherry | | 2010/0211052 A1 | 8/2010 | Brown et al. |
| 2004/0044395 A1 | 3/2004 | Nelson | | 2010/0331958 A1 | 12/2010 | Chobotov |
| 2004/0049212 A1 | 3/2004 | Whayne | | 2011/0218609 A1 | 9/2011 | Chobotov et al. |
| 2004/0049264 A1 | 3/2004 | Sowinski et al. | | | | |
| 2004/0093055 A1 | 5/2004 | Bartorelli et al. | | FOREIGN PATENT DOCUMENTS | | |
| 2004/0093064 A1 | 5/2004 | Bosma | | EP | 0714641 | 6/1996 |
| 2004/0093068 A1 | 5/2004 | Bergen et al. | | EP | 0775472 | 5/1997 |
| 2004/0093078 A1 | 5/2004 | Moll et al. | | EP | 0792627 | 9/1997 |
| 2004/0098096 A1 | 5/2004 | Eton | | EP | 0808613 | 11/1997 |
| 2004/0106974 A1 | 6/2004 | Greenberg et al. | | EP | 0819411 | 1/1998 |
| 2004/0116997 A1 | 6/2004 | Taylor et al. | | EP | 0943302 | 9/1999 |
| 2004/0138734 A1 | 7/2004 | Chobotov et al. | | EP | 0997115 | 5/2000 |
| 2004/0162607 A1 | 8/2004 | Masroor | | EP | 0480667 | 4/2001 |
| 2004/0167614 A1 | 8/2004 | Anson | | EP | 1093772 | 4/2001 |
| 2004/0210304 A1 | 10/2004 | Seguin et al. | | EP | A 1138280 | 10/2001 |
| 2004/0215213 A1 | 10/2004 | Dolan | | EP | 0808140 | 12/2001 |
| 2004/0220655 A1 | 11/2004 | Swanson et al. | | EP | 1163991 | 12/2001 |
| 2004/0220664 A1 | 11/2004 | Chobotov | | EP | 1212991 | 6/2002 |
| 2004/0254625 A1 | 12/2004 | Stephens | | EP | 1266636 | 12/2002 |
| 2005/0033406 A1 | 2/2005 | Barnhart et al. | | EP | 1380270 | 1/2004 |
| 2005/0049691 A1 | 3/2005 | Mericle et al. | | EP | 1415617 | 4/2004 |
| 2005/0058920 A1 | 3/2005 | Tokarski et al. | | JP | 49 042773 | 4/1974 |
| 2005/0075715 A1 | 4/2005 | Borges et al. | | JP | 3109404 | 5/1991 |
| 2005/0090804 A1 | 4/2005 | Chobotov et al. | | JP | 5161665 | 6/1993 |
| 2005/0090901 A1 | 4/2005 | Studer | | JP | 6100054 | 4/1994 |
| 2005/0158272 A1 | 7/2005 | Whirley et al. | | JP | 09117511 | 5/1997 |
| 2005/0171593 A1 | 8/2005 | Whirley et al. | | JP | 18-126862 | 6/2006 |
| 2005/0177222 A1 | 8/2005 | Mead | | JP | 18-136382 | 6/2006 |
| 2005/0222669 A1 | 10/2005 | Purdy | | RU | 2029527 | 2/1995 |

| | | |
|---|---|---|
| SU | 1217402 | 3/1986 |
| SU | 1237201 | 6/1986 |
| SU | 1237202 | 6/1986 |
| SU | 1273077 | 11/1986 |
| SU | 1342511 | 10/1987 |
| SU | 1389778 | 4/1988 |
| SU | 1457921 | 2/1989 |
| SU | 1482714 | 5/1989 |
| SU | 1560134 | 4/1990 |
| SU | 1586718 | 8/1990 |
| SU | 1650127 | 5/1991 |
| SU | 1732964 | 5/1992 |
| SU | 1768154 | 10/1992 |
| SU | 1812980 | 4/1993 |
| WO | WO 91/00792 | 1/1991 |
| WO | WO 92/22604 | 12/1992 |
| WO | WO 93/13824 | 7/1993 |
| WO | WO 93/19804 | 10/1993 |
| WO | WO 94/03127 | 2/1994 |
| WO | WO 95/03754 | 2/1995 |
| WO | WO 95/09586 | 4/1995 |
| WO | WO 96/14095 | 5/1996 |
| WO | WO 96/14808 | 5/1996 |
| WO | WO 97/07751 | 3/1997 |
| WO | WO 97/29716 | 8/1997 |
| WO | WO 98/06355 | 2/1998 |
| WO | WO 98/38947 | 9/1998 |
| WO | WO 98/41167 | 9/1998 |
| WO | WO 98/44870 | 10/1998 |
| WO | WO 98/44873 | 10/1998 |
| WO | WO 99/00073 | 1/1999 |
| WO | WO 99/26559 | 6/1999 |
| WO | WO 99/38455 | 8/1999 |
| WO | WO 99/43378 | 9/1999 |
| WO | WO 99/43379 | 9/1999 |
| WO | WO 00/10487 | 3/2000 |
| WO | WO 00/13613 | 3/2000 |
| WO | WO 00/42947 | 7/2000 |
| WO | WO 00/42948 | 7/2000 |
| WO | WO 00/44808 | 8/2000 |
| WO | WO 00/51522 | 9/2000 |
| WO | WO 00/67675 | 11/2000 |
| WO | WO 00/71179 | 11/2000 |
| WO | WO 01/05331 | 1/2001 |
| WO | WO 01/08599 | 2/2001 |
| WO | WO 01/15633 | 3/2001 |
| WO | WO 01/21108 | 3/2001 |
| WO | WO 01/30270 | 5/2001 |
| WO | WO 01/41675 | 6/2001 |
| WO | WO 01/56500 | 8/2001 |
| WO | WO 01/56504 | 8/2001 |
| WO | WO 01/58384 | 8/2001 |
| WO | WO 01/58387 | 8/2001 |
| WO | WO 01/66037 | 9/2001 |
| WO | WO 01/67993 | 9/2001 |
| WO | WO 01/74270 | 10/2001 |
| WO | WO 01/82836 | 11/2001 |
| WO | WO 02/36332 | 5/2002 |
| WO | WO 02/41804 | 5/2002 |
| WO | WO 02/078569 | 10/2002 |
| WO | WO 02/083038 | 10/2002 |
| WO | WO 02/100454 | 12/2002 |
| WO | WO 03/022180 | 3/2003 |
| WO | WO 03/053287 | 7/2003 |
| WO | WO 03/094795 | 11/2003 |
| WO | WO 03/094799 | 11/2003 |
| WO | WO 2004/002370 | 1/2004 |
| WO | WO 2004/002371 | 1/2004 |
| WO | WO 2004/017866 | 3/2004 |
| WO | WO 2004/078065 | 9/2004 |
| WO | WO 2005/086942 | 9/2005 |
| WO | WO 2009/042796 | 4/2009 |
| WO | WO 2009/086200 | 7/2009 |
| WO | WO 2011/100367 | 8/2011 |

OTHER PUBLICATIONS

The AneuRx® Stent Graft Treatment for TAA brochure, "An Endoluminal Solution for the Treatment of Descending Thoracic Aortic Aneurysms," Medtronic, Inc. 1999.

Blum et al. "Abdominal aortic aneurysms: preliminary technical and clinical results with transfemoral placement of endovascular self-expanding stent-grafts" Radiology 198(1):25-31 (1996). ;198(1):25-31 (1996).

Blum et al. "Endoluminal stent-grafts for infrarenal abdominal aortic aneurysms" N Engl J Med 336(1):13-20 (1997). ;336(1):13-20 (1997).

Campbell et al., "Balloon-Artery Interactions During Stent Placement: A Finite Element Analysis Approach to Pressure, Compliance, and Stent Design as Contributors to Vascular Injury"; 1999; American Heart Association; pp. 378-383.

Canero et al., "Optimal stent implantation: three-dimensional evaluation of the mutual position of stent and vessel via intracoronary echocardiography," Computers in Cardiology, 261-264 (Sep. 1999).

Cooley, Denton A., Surgical Treatment of Aortic Aneurysms (Book), W.B. Saunders Company, West Washington Square, PA (1986).

Donayre, et al., "Fillable endovascular aneurysm repair", Endovascular Today, p. 64-66, Jan. 2009.

Dumoulin C. et al., "Mechanical behavior modeling of balloon expandable stents." Journal of Biomechanics, vol. 33, No. 11, pp. 1461-1470 (available online: Sep. 8, 2000).

Elger et al. "The Influence of Shape on the Stresses in Model Abdominal Aortic Aneurysms," Transactions of the ASME 326:326-32 (1996).

Ernst "Current therapy for infrarenal aortic aneurysms" N Engl J Med 336(1):58-60 (1997).

Haimovitch, L. and Patierson, N., "Robust growth is forecast for endovascular repair of AAAs," The BBI Newsletter, vol. 26, No. 5, pp. 113-144, (May 2003).

How et al. "Mechanical Properties of Arteries and Arterial Grafts," Chapter 1 of Cardiovascular Biomaterials Hasting, G.W. (ed.) London; New York: Springer-Verlag, 1992 pp. 1-35.

Lakshmiraghavan, M. Mechanical Wall Stress in Abdominal Aortic Aneurysm: Towards the Development of a Clinical Tool to Predict Aneurysm Rupture. Submitted to the University of Pittsburgh, vol. 59/09-B of Dissertation Abstracts International p. 4948. 285 pages (1998).

Mandai, S. et al. (1992). "Direct Thrombosis of Aneurysms with Cellulose Acetate Polymer. Part I: Results of Thrombosis in Experimental Aneurysms," J. Neurosurgery 77:497-500.

Mirich et al., "Percutaneously Placed Endovascular Grafts for Aortic Aneurysms: Feasibility Study", Radiology, 170/3:1033-1037 (1989); 1033-1037 (1989).

Moore et al. "Transfemoral endovascular repair of abdominal aortic aneurysm: results of the North American EVT phase 1 trial" J Vasc Surg 23(4):543-553 (1996). ;23(4):543-553 (1996).

Mower et al. "Stress Distributions in Vascular Aneurysms: Factors Affecting Risk of Aneurysm Rupture," J. Surgical Research 55:151-61 (1993).

Office Action mailed: Oct. 1, 2009 in U.S. Appl. No. 11/861,731, filed Sep. 26, 2007 and published as: US2009/0082847 on Mar. 26, 2009.

Parodi "Endovascular repair of abdominal aortic aneurysms and other arterial lesions" J Vasc Surg 21(4):549-557 (1995).;21(4):549-557 (1995).

Parodi et al., "Transfemoral intraluminal graft implantation for abdominal aortic aneurysms," Ann. Vasc. Surg., 5(6):491-499 (1991).

Perry, M. D. and Chang, R. T., "Finite Element Analysis of NI-TI Alloy Stent Deployment," Proceedings of the Second International Conference on SMST, Asilomar Conference Center, Pacific Grove CA. USA (1997).

Rogers et al., "Balloon-Artery Interactions During Stent Placement: A finite element analysis approach to pressure, compliance and stent design as contributors to vascular injury", 1999 American Heart Association pp. 378-383.

Stern et al., "Interactive Definition of Endoluminal Aortic Stent Size and Morphology Based on Virtual Angioscopic Rendering of 3D Magnetic Resonance Angiography (MRA)," Cars. Computer Assisted Radiology and Surgery, Proceedings of the International Symposium on Computer Assisted Radiology and Surgery:176-180 (Jun. 1999).

Uflacker, R. and Robinson, J., "Endovascular treatment of abdominal aortic aneurysms: a review," Eur. Radial.,11:739-753 (2001).

Verhagen "Latest AAA Innovations: The Endurant Stent Graft System", Veith Symposium Nov. 17, 2007.

Verhagen, Hence J.M. "Endurant Medtronic Endograft for EVAR: advantages & early experience", Slides from Veith Symposium Presentation Nov. 22, 2008.

Vos, A.F.W. et al., "Endovascular Grafting of Complex Aortic Aneurysms with a modular site Branch Stent Graft System in a Porcine Model", Eur J Vasc Endovasc Surg, May 2004 vol. 27 492-497.

Volodos, N.L. et al. (1987). "New Balloon Catheter for Dilating Arteries and Installing Prosthesis During Distal Endoprosthetics With Self-Fixing Synthetic Prosthesis," *Thesis of VIII Symposium* (Oct. 8-10, 1987), Abstract Only in English, four pages.

Volodos, N.L. et al. (1986) "Self-Fixing Synthetic Prostheisis for Endoprosthesis of Vessels," Vestnik Khigurgii pp. 123-124, Abstract Only in English.

Volodos, N.L. et al. (1989). "Clinical Experience in Use of Self-Fixing Synthetic Prosthesis for Distal and Intraoperative Endoprosthestics of Aora and Iliac Arteries," Theses of Ixth All-Union Symposium (Oct. 2-3, 1989), Abstract only in English, four pages.

Web page, "Drug Eluting Stents—Why Use Drug Eluting Stents?" Polymer Coatings Division; at: URL http://www.lombardmedlcal.co.uk/lombard/pcde.why.html; Lombard Medical; printed Feb. 1, 2005.

Whitcher, "Simulation of in vivo loading conditions of nitinol vascular stent structures", 1997, Elsevier Science Ltd., pp. 1005-1011.

Whitcher, F., "A Finite Element Treatment of the In-Vivo Loading Conditions of NITI AD Vascular Stent and Graft Structures," Proceedings of the Second International Conference on SMST, Asilomar Conference Center, Pacific Grove. CA, USA (1997).

Wisselink, W. et al. (2001). "Clipping of Inferior Mesenteric and Lumbar Arteries via Retroperitoneal Laparo-Endoscopic Approach as a Treatment of Persistent Endoleak" Chapter 18 in Endoleaks and Endotension, Veith, F.J. et al. eds. Marcel Dekker, Inc. pp. 211-220.

Extended European Search Report Mailed Dec. 16, 2009 in European Application No. 09175398.8 filed: Oct. 15, 2004 and published as: EP 2145607 on Jan. 20, 2010.

International Preliminary Report on Patentability mailed on Apr. 15, 2010 for International Application No. PCT/US2008/078846 filed on Oct. 3, 2008 and published as WO/2009/046372 on Apr. 9, 2009.

International Search Report and Written Opinion mailed on Jul. 30, 2009 for International Application No. PCT/US2008/078846 filed on Oct. 3, 2008 and published as WO/2009/046372 on Apr. 9, 2009.

International Preliminary Report on Patentability mailed on Apr. 8, 2010 for International Application No. PCT/US2008/077714 filed on Sep. 25, 2008 and published as WO/2009/042789 on Apr. 2, 2009.

International Search Report and Written Opinion mailed on: May 1, 2009 for International Application No. PCT/US2008/077714 filed on Sep. 25, 2008 and published as WO/2009/042789 on Apr. 2, 2009.

International Preliminary Report on Patentability mailed on May 27, 2010 for International Application No. PCT/US2008/083451 filed on Nov. 13, 2008 and published as WO/2009/064923 on May 22, 2009.

International Search Report and Written Opinion mailed on Jun. 30, 2009 for International Application No. PCT/US2008/083451 filed on Nov. 13, 2008 and published as WO/2009/064923 on May 22, 2009.

International Search Report and Written Opinion mailed on Mar. 26, 2009 for International Application No. PCT/US2008/077727 filed on Sep. 25, 2008 and published as WO2009/042796 on Apr. 2, 2009.

International Preliminary Report on Patentability mailed on Apr. 8, 2010 for International Application No. PCT/US2008/077727 filed on Sep. 25, 2008 and published as WO2009/042796 on Apr. 2, 2009.

Office Action mailed: Jan. 14, 2010 in U.S. Appl. No. 11/861,739, filed Sep. 26, 2007 and published as: US2009/0082841 on Mar. 26, 2009.

Office Action Response mailed Jun. 14, 2010 in U.S. Appl. No. 11/861,739, filed Sep. 26, 2007 and published as: US2009/0082841 on Mar. 26, 2009.

Office Action Response mailed: Jan. 4, 2010 in U.S. Appl. No. 11/861,731, filed Sep. 26, 2007 and published as: US2009/0082847 on Mar. 26, 2009.

Office Action mailed: Apr. 14, 2010 in U.S. Appl. No. 11/861,731, filed Sep. 26, 2007 and published as: US2009/0082847 on Mar. 26, 2009.

Extended European Search Report Mailed Jul. 27, 2010 in European Application No. 10005904.7 filed: Apr. 11, 2002 and published as: EP 2221023 on Aug. 25, 2010.

International Preliminary Report on Patentability mailed on Jul. 1, 2010 for International Application No. PCT/US2008/087831 filed on Dec. 19, 2008 and published as WO/2009/086200 on Jul. 9, 2009.

International Search Report and Written Opinion mailed on May 28, 2009 for International Application No. PCT/US2008/087831 filed on Dec. 19, 2008 and published as WO/2009/086200 on Jul. 9, 2009.

Office Action Response mailed: Jul. 18, 2011 in U.S. Appl. No. 12/245,620, filed Oct. 3, 2008 and published as: US2009/0099649 on Apr. 16, 2009.

Office Action mailed: Jan. 19, 2011 in U.S. Appl. No. 12/245,620, filed Oct. 3, 2008 and published as: US2009/0099649 on Apr. 16, 2009.

Office Action Response mailed: Nov. 12, 2010 in U.S. Appl. No. 12/245,620, filed Oct. 3, 2008 and published as: US2009/0099649 on Apr. 16, 2009.

Office Action mailed: May 14, 2010 in U.S. Appl. No. 12/245,620, filed Oct. 3, 2008 and published as: US2009/0099649 on Apr. 16, 2009.

International Search Report and Written Opinion mailed on Oct. 31, 2011 for International Application No. PCT/US2011/024248 filed on Feb. 9, 2011 and published as WO/2011/100367 on Aug. 28, 2011.

Office Action mailed on Nov. 28, 2011 in U.S. Appl. No. 12/747,499, filed Sep. 7, 2010 and published as: US2010/0331958 on: Dec. 30, 2010.

Office Action mailed: Mar. 13, 2012 in U.S. Appl. No. 11/861,731, filed Sep. 26, 2007 and published as: US2009/0082847 on Mar. 26, 2009.

US 6,413,270, 07/2002, Thornton et al. (withdrawn)

* cited by examiner

STENT AND DELIVERY SYSTEM FOR DEPLOYMENT THEREOF

BACKGROUND OF THE INVENTION

This invention relates generally to endoluminal devices, particularly stents and grafts for placement in an area of a body lumen that has been weakened by damage or disease, such as an aneurysm of the abdominal aorta, and more particularly to a stent and a corresponding system for deployment thereof.

Medical devices for placement in a human or other animal body are well known in the art. One class of medical devices comprises endoluminal devices such as stents, stent-grafts, filters, coils, occlusion baskets, valves, and the like. A stent typically is an elongated device used to support an intraluminal wall. In the case of a stenosis, for example, a stent provides an unobstructed conduit through a body lumen in the area of the stenosis. Such a stent may also have a prosthetic graft layer of fabric or covering lining the inside and/or outside thereof. A covered stent is commonly referred to in the art as an intraluminal prosthesis, an endoluminal or endovascular graft (EVG), a stent-graft, or endograft.

An endograft may be used, for example, to treat a vascular aneurysm by removing or reducing the pressure on a weakened part of an artery so as to reduce the risk of rupture. Typically, an endograft is implanted in a blood vessel at the site of a stenosis or aneurysm endoluminally, i.e. by so-called "minimally invasive techniques" in which the endograft, typically restrained in a radially compressed configuration by a sheath, crocheted or knit web, catheter or other means, is delivered by an endograft delivery system or "introducer" to the site where it is required. The introducer may enter the vessel or lumen from an access location outside the body, such as purcutaneously through the patient's skin, or by a "cut down" technique in which the entry vessel or lumen is exposed by minor surgical means.

Figure 1:
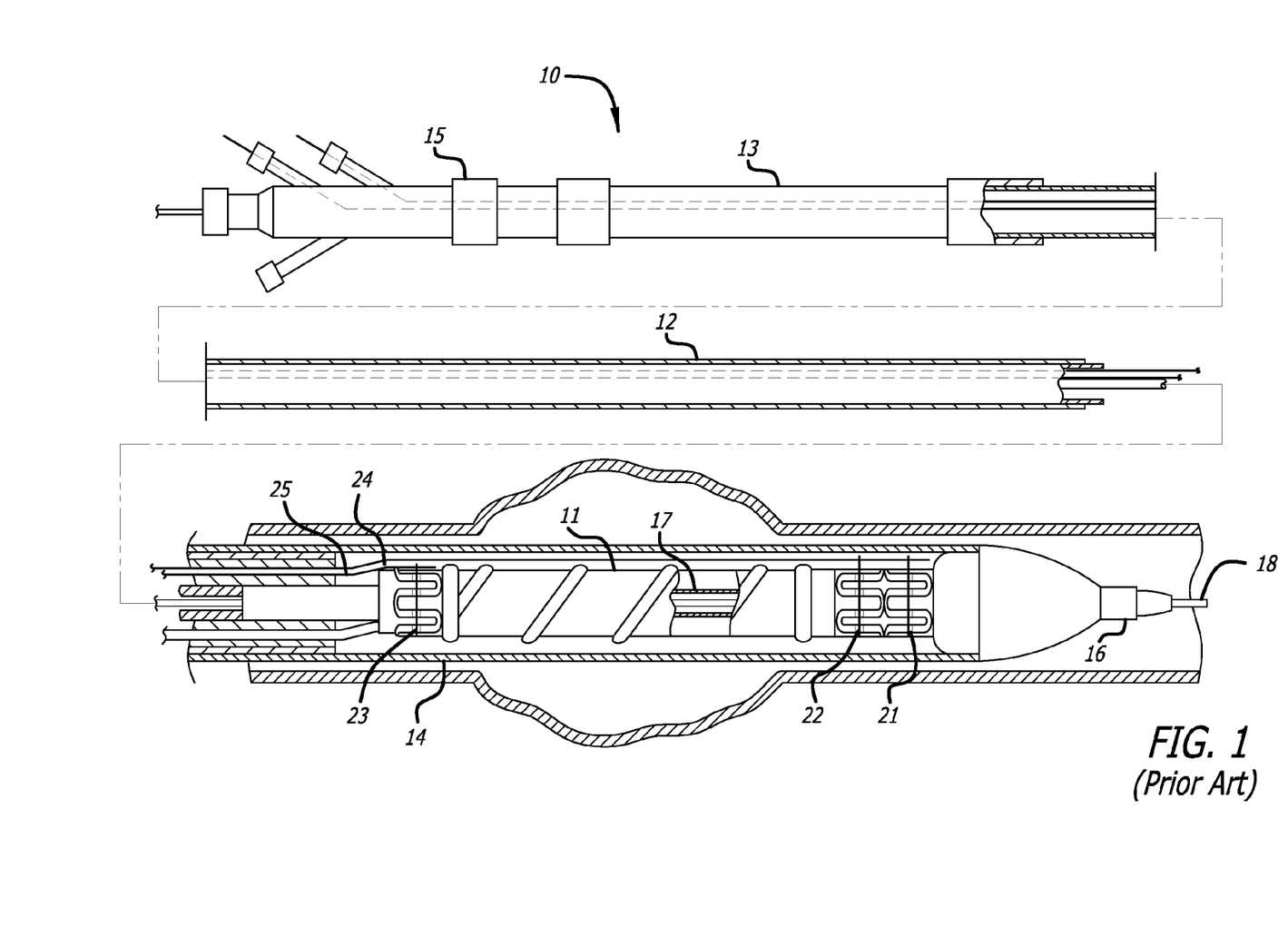
FIG. 1 is a side elevation view in partial section of a prior art endovascular stent graft delivery system.

U.S. Patent Application Publication No. US 2004/0138734, which is incorporated herein in its entirety by reference, describes systems and methods for the delivery of stents, endovascular grafts, and the like. FIG. 1 herein illustrates a delivery system 10 of such publication for delivering a variety of expandable intracorporeal devices; for example, an expandable endovascular graft 11. One such expandable endovascular graft 11 useful for delivery and deployment at a desired site within a patient is disclosed in U.S. Pat. No. 6,395,019, which is hereby incorporated by reference in its entirety.

Delivery system 10 in FIG. 1 has an elongate shaft 12 with a proximal section 13, a distal section 14, a proximal end 15 and a distal end 16. The distal section 14 has an elongate belt support member in the form of a guidewire tube 17 disposed adjacent a portion of the expandable endovascular graft 11. A guidewire 18 is disposed within guidewire tube 17. A plurality of belts 21, 22, and 23 are secured to the guidewire tube 17 and are circumferentially disposed about portions of the endovascular graft 11. FIG. 1 shows the belts in a configuration that constrains the endovascular graft 11. First and second release members 24 and 25 releasably secure belts 21, 22, and 23 in a constraining configuration as shown.

As defined herein, the proximal end of the elongate shaft is the end 15 proximal to an operator of the delivery system 10 during use. The distal end of the elongate shaft is the end 16 that enters and extends into the patient's body. The proximal and distal directions for the delivery system 10 and endovascular graft 11 loaded within the delivery system 10 as used herein are the same. This convention is used throughout the specification for the purposes of clarity, although other conventions are commonly used.

Belts 21-23 extend circumferentially about the respective portions of the expandable intracorporeal device 11 and are releasably locked together by one or more release members 24 and 25. U.S. Patent Application Publication No. US 2004/0138734 discloses various belt and release wire configurations that may be utilized to secure stents and the like.

To deploy the graft 11, the release wires 24 and 25 are pulled proximally, in a desired sequence, such that the release wires 24 and 25 disengage from the end loops of the belts 21, 22 and 23. It is desired to provide a system and method to minimize the axial force required on the release wires 24 and 25 to release the belts 21, 22 and 23.

SUMMARY OF THE INVENTION

In one aspect, the present invention may provide a stent comprising a plurality of substantially axially extending struts; and an extension coupled to one of the struts and extending circumferentially therefrom to a free end, thereby defining a shoulder surface at angle approximately 90° or less relative to a longitudinal axis of the stent strut.

In another aspect, the invention may provide a stent delivery system comprising a delivery shaft and a stent configured to be positioned about the delivery shaft. The stent includes an extension extending circumferentially from a portion of the stent to a free end, thereby defining a shoulder surface. A belt has a first portion fixed relative to the delivery shaft and a second portion positioned circumferentially about at least a portion of the stent to retain the stent in an at least partially constrained configuration. A release wire is configured to releasably engage at least a portion of the belt to retain the belt. The shoulder surface engages at least a portion of the belt to minimize axial movement of the belt during release of the release wire from engagement with the belt.

In yet another aspect, the invention may provide a method of assembling a stent on a stent delivery shaft, the method comprising fixing a first portion of a belt relative to the delivery shaft; positioning a stent about a portion of the delivery shaft; positioning a second portion of the belt circumferentially about at least a portion of the stent to retain the stent in a constrained configuration; engaging at least a portion of the belt with a release wire to maintain the belt about the stent; and engaging at least a portion of the belt with an extension extending circumferentially from a portion of the stent and defining a shoulder surface.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 2:
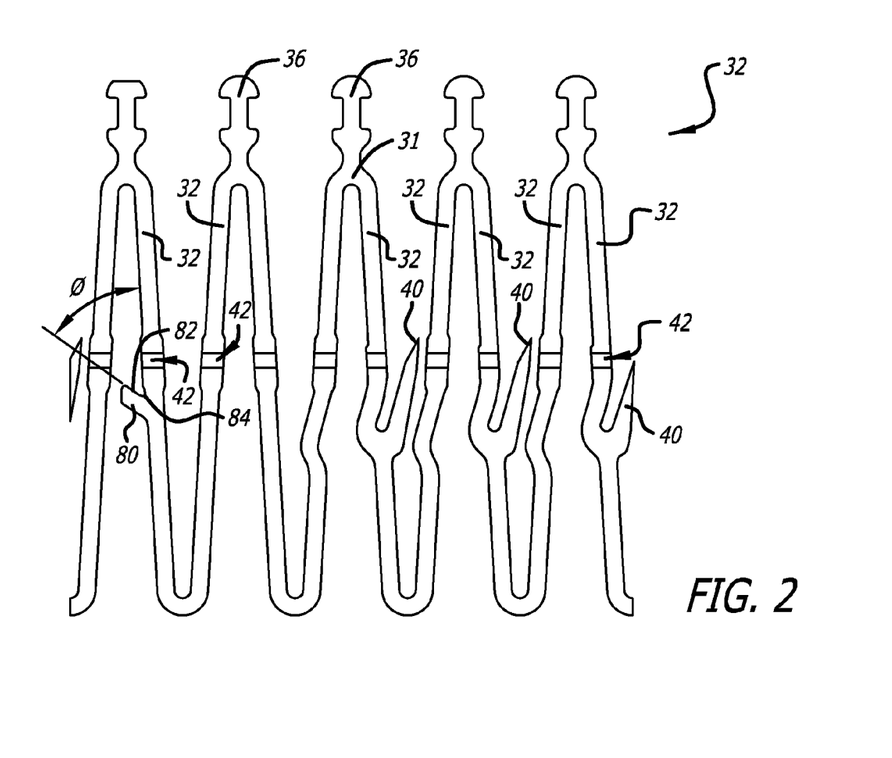
FIG. 2 shows a flat pattern of an embodiment of a stent in accordance with one or more aspects of the invention.

Referring to FIG. 2, a stent 30 that is a first embodiment of the present invention is illustrated. Stent 30 includes a plurality of struts 32 extending axially between the opposed ends 31, 33 thereof. The stent 30 can be oriented in either direction, that is, the end 33 may represent the proximal end or the distal end of the stent 30, depending on the application. Both ends 31, 33 have a plurality of crowns adjoining adjacent struts 32. The end 33 of stent 30 has a plurality of connecting members 36 configured to connect the stent 30 to a graft or other structure. The illustrated stent 30 structure is merely a representative example, and the invention is not intended to be limited to such. The stent 30 of the present invention can have various structures and is not limited to the strut structure illustrated herein. For example, the stent 30 may have a body defined by a lattice structure or a helical structure.

Along one or more of the struts 32, a barb 40 may be provided. The barbs 40 are preferably formed integrally with the struts 32, but may otherwise be manufactured, for example, as a separate component attached to the struts 32. The stent struts 32 and the barbs 40 are preferably self expanding, that is, upon release of a constraining force, the struts 32 will move radially apart and the barbs 40 will extend radially outward. Other configurations, for example, balloon expansion, are also contemplated within the present invention.

Figure 3:
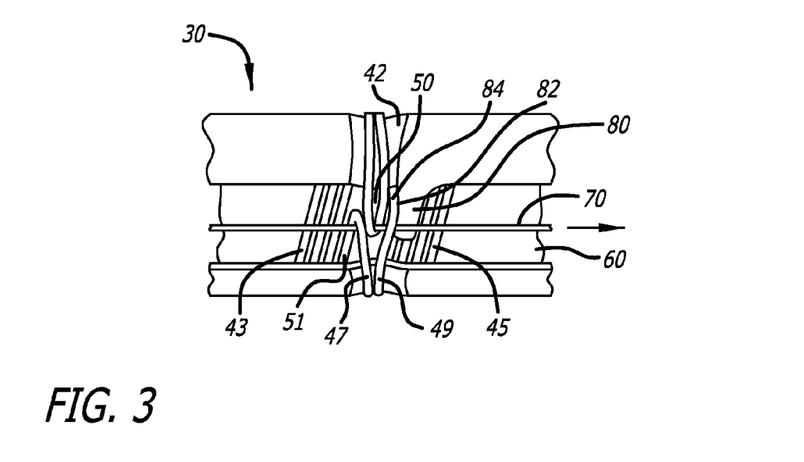
FIG. 3 is a side elevation view illustrating the stent of FIG. 2 positioned about an embodiment of a delivery system in accordance with one or more aspects of the invention.
Figure 4:
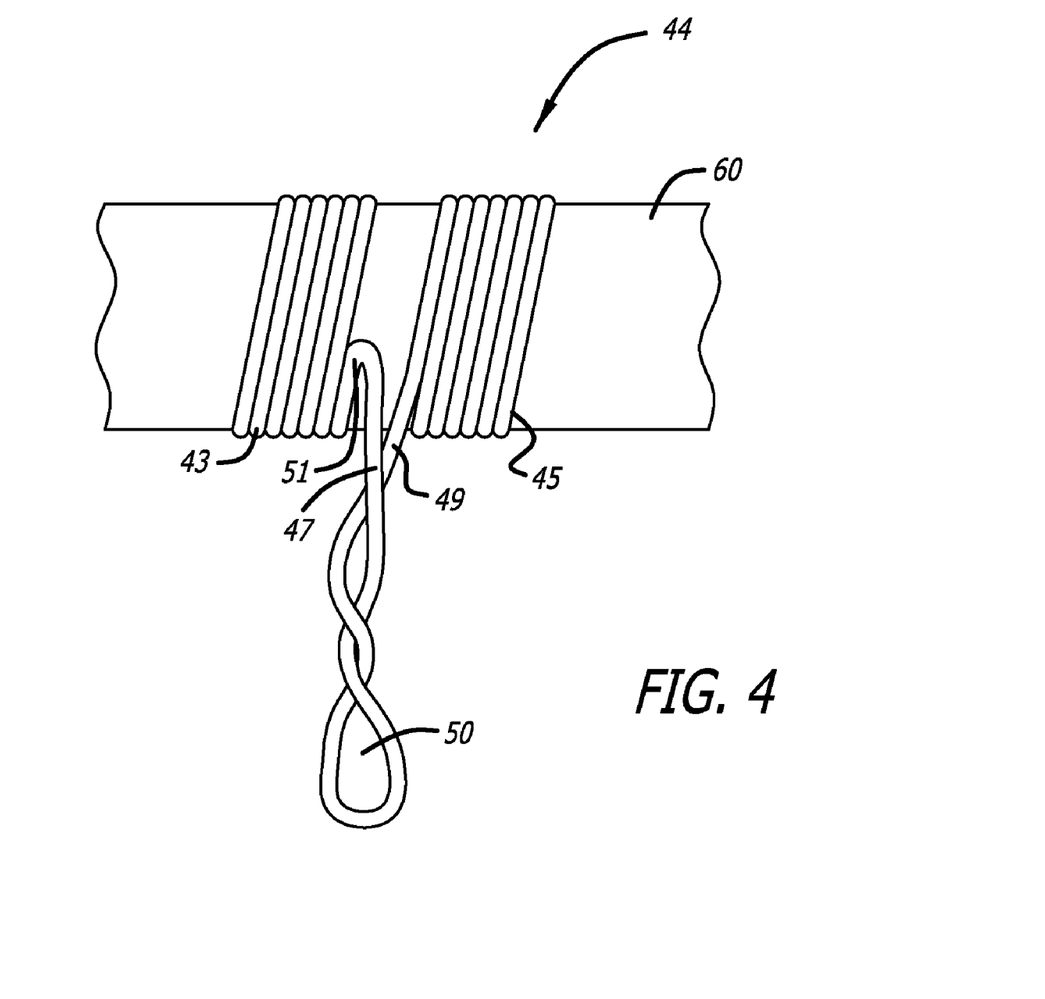
FIG. 4 is a side elevation view illustrating an embodiment of a delivery shaft with a belt positioned thereabout.

Referring to FIGS. 3 and 4, a belt 44 is positioned about the stent 30 and secured to maintain the stent 30 in at least a partially constrained configuration. In the present embodiment, opposite ends 43 and 45 of the belt 44 are separately wrapped about the delivery shaft 60. Both ends 43 and 45 are secured to the delivery shaft 60, for example, via adhesive, welding, bonding or any other suitable means. Two intermediate belt portions 47 and 49 extend from the bonded portions and are intertwined to define an eye loop 50 at a free portion of the belt 44 configured to receive a release wire 70 to maintain the stent 30 in the at least a partially constrained configuration. As illustrated in FIGS. 3 and 4, in the present embodiment, intermediate belt portion 47 is returned upon itself to form a partial loop portion 51 through which the release wire 70 extends. Intermediate belt portion 49 extends tangentially from the delivery shaft 60 and extends over the release wire 70.

While the release wire 70 is illustrated as engaging only one belt, the release wire 70 may extend through multiple stent belts 44 or a single stent belt 44. Various belt and release wire configurations and sequences are described in U.S. Patent Application Publication No. US 2004/0138734, which is incorporated herein in its entirety by reference.

To provide general axial containment of the belt 44, a circumferential groove 42 is preferably ground about the stent 30. While the groove 42 provides general axial containment, belts of prior art systems have been found to move in conjunction with the release wire due to the friction force created between the belt and the release wire. The friction force may provide undesired resistance to removal of the release wire. Such undesired resistance to removal of the release wire may be further enhanced if a portion of the belt moves axially, thereby creating a pivot motion which may pinch or otherwise trap the release wire.

Referring to FIGS. 2 and 3, the stent 30 of the present embodiment of the invention includes an extension 80 extending circumferentially from one of the struts 32 to define a shoulder surface 82. In the present embodiment, the extension 80 is formed integrally with the strut 32 during stamping of the stent 30. Provision of the extension 80 on the stent 30 allows the extension 80 to be accurately positioned relative to the intended position of the belt 44. In the present embodiment, the shoulder surface 82 is positioned slightly proximal of the groove 42. The shoulder surface 82 preferably extends at an angle Ø relative to the longitudinal axis of the strut. With such an arrangement, the shoulder surface 82 guides the belt 44 toward the junction 84 between the shoulder surface 82 and the strut 32 and reduces the changes the belt 44 will slip past the extension 80 in the proximal direction.

Referring to FIG. 3, it is preferable that the extension 80 is provided on the strut 32 which is the last strut 32 that the free portion of the belt 44 passes over. As such, the eye loop 50 positioned about the release wire 70 biases the release wire 70 toward the extension 80, thereby moving the intermediate portion 49 toward the shoulder surface 82. However, the extension 80 may be provided on any of the other struts 32 if such will be aligned adjacent the release wire 70.

As further illustrated in FIG. 3, it is also preferable that the extension 80 be axially positioned such that it is proximally adjacent the intermediate belt portion 49 which extends tangentially from the delivery shaft 60 as opposed to the intermediate belt portion 47 that is returned upon itself. With such an arrangement, the intermediate belt portion 49 extends from under the strut 32 over the release wire such that it crosses the shoulder surface 82. However, the extension 80 may be otherwise axially positioned. For example, in the embodiment illustrated in FIG. 6, the extension 80' is positioned axially adjacent the returned intermediate belt portion 47, however, the extension 80' still contacts the eye loop 50 and maintains the axial position of the belt 44.

The belt 44 can be made from any high strength, resilient material that can accommodate the tensile requirements of the belt members and remain flexible after being set in a constraining configuration. Typically, belt 44 is made from solid ribbon or wire of a shape memory alloy such as nickel titanium or the like, although other metallic or polymeric materials are possible. Belt 44 may also be made of braided metal filaments or braided or solid filaments of high strength synthetic fibers such as Dacron®, Spectra or the like. The release wire 70 is generally made from a biocompatible high strength alloy such as stainless steel, but can also be made from any other suitable materials. Examples include other metallic alloys such as nickel titanium, non-metallic fibers such as carbon, polymeric materials, composites thereof, and the like. The diameter and stiffness of the release wire 70 can be selected in accordance with the diameter and stiffness of the belt 44. The configuration of the belt 44 may vary to suit the particular embodiment of the delivery system. As set forth above, various belt and release wire configurations and sequences are described in U.S. Patent Application Publication No. US 2004/0138734, which is incorporated herein in its entirety by reference.

The delivery shaft 60 illustrated herein may have various configurations. For example, the delivery shaft 60 may be a catheter, a guide wire lumen, a solid shaft or any other suitable structure. Similarly, while the belts 44 are illustrated as directly connected to the delivery shaft 60 without any additional support, belt bushings, standoff tubes and the like may be provided to secure, support and direct the belt 44.

Figure 5:
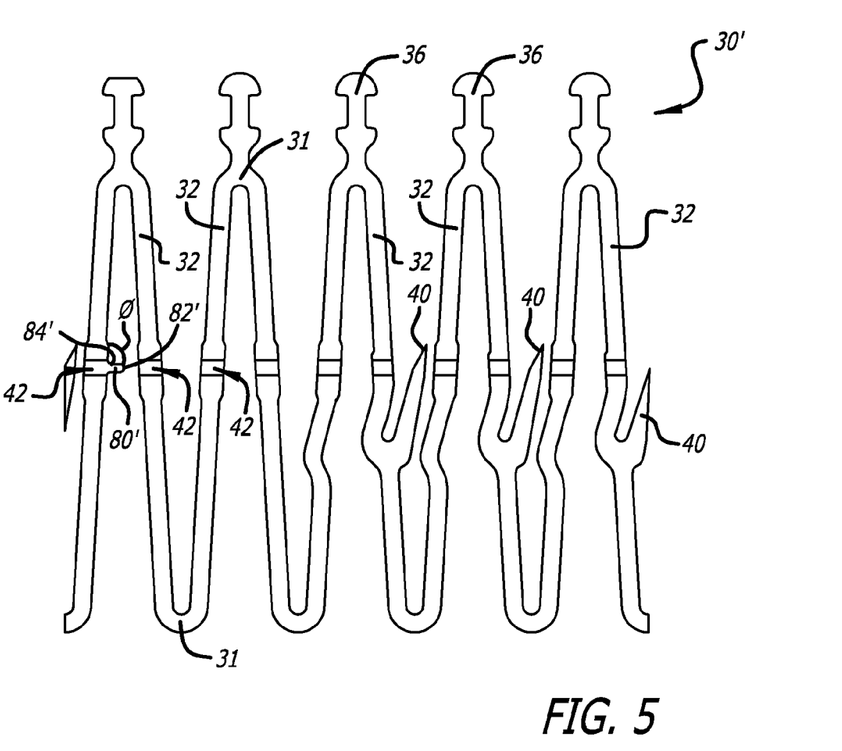
FIG. 5 shows a flat pattern of an alternative embodiment of a stent in accordance with one or more aspects of the invention.
Figure 6:
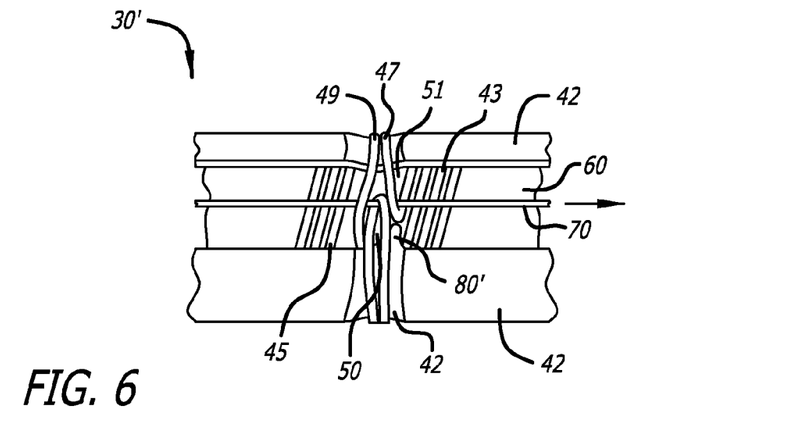
FIG. 6 is a side elevation view illustrating the stent of FIG. 5 positioned about an embodiment of a delivery system in accordance with one or more aspects of the invention.

Referring to FIGS. 5 and 6, a stent 30' that is an alternative embodiment of the present invention is shown. The stent 30' is similar to the previous embodiment and like elements are numbered alike. Stent 30' includes a extension 80' that is formed integrally formed with the strut 32 axially aligned with the groove 42 such that the shoulder surface 82' is within the axial confines of the groove 42. Additionally, the shoulder surface 82' is at angle Ø which is substantially perpendicular to the strut 32. The junction 84' is still configured to receive a portion of the belt 44. As explained above with respect to FIG. 6, the extension 80' is positioned axially adjacent the returned intermediate belt portion 47, however, the extension 80' still contacts the eye loop 50 and maintains the axial position of the belt 44. The extension 80' has a circumferential length such that the extension 80' does not pass under the release wire 70, but instead terminates prior to reaching the release wire 70.

Figure 7:
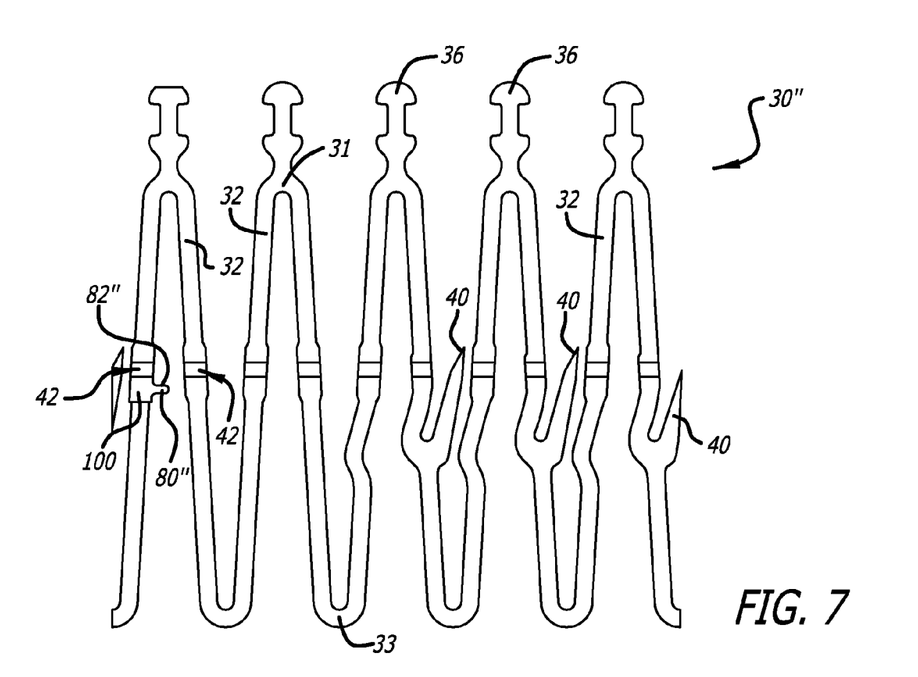
FIG. 7 shows a flat pattern of another alternative embodiment of a stent in accordance with one or more aspects of the invention.

Referring to FIG. 7, a stent 30" that is an another alternative embodiment of the present invention is shown. The stent 30" is similar to the previous embodiments and like elements are numbered alike. Stent 30" includes a extension 80". The extension 80" is formed as part of a separate shoulder member 100 that is interconnected with the strut 32. The shoulder member 100 may be crimped, adhered, welded, bonded or otherwise fixed relative to the strut 32. The shoulder member 100 is axially aligned such that the shoulder surface 82" is axially aligned in a desired relationship with respect to the groove 42. In the illustrated embodiment, the contact face 82" is aligned directly with an axial edge of the groove 42 and the shoulder surface 82" is at angle Ø which is substantially perpendicular to a longitudinal axis of the strut 32. The position of the extension 80" relative to the intermediate belt portions 47 and 49 can be controlled by positioning the shoulder member 100 prior to interconnection and/or by controlling the direction of winding of the belt 44 with respect to the delivery shaft 60.

What is claimed:

1. A stent comprising:
    a plurality of struts extending in a substantially axial direction from respective proximal ends to respective distal ends thereof along respective longitudinal axes thereof;
    a belt groove which extends circumferentially about the plurality of struts between the proximal ends and distal ends of the plurality of struts and which includes a distal edge that is closer to the distal ends of the struts than the proximal ends of the struts and a proximal edge which is closer to the proximal ends of the struts than the distal ends of the struts; and
    an extension extending circumferentially from a strut to a free end of the extension, the extension including a shoulder surface which is configured to engage a belt disposed in the belt groove, the shoulder surface extending from the strut to the free end of the extension such that the shoulder surface and a junction between the shoulder surface and the strut are disposed between the proximal edge of the belt groove and the distal edge of the belt groove and the shoulder surface being disposed at an angle of approximately 90° relative to a longitudinal axis of the strut.

2. The stent of claim 1 wherein the extension is formed integrally with the strut.

3. The stent of claim 1 wherein the extension is formed as part of a separate shoulder member that is interconnected with the strut.

4. The stent of claim 3 wherein the shoulder member is interconnected with the strut via crimping, adhesion, welding or bonding.

5. The stent of claim 1 wherein the shoulder surface is axially adjacent to the belt groove proximal edge.

6. The stent of claim 1 wherein the free end of the extension comprises a blunted configuration.

7. A stent delivery system comprising:
    a delivery shaft;
    a stent configured to be positioned about the delivery shaft, the stent including:
        a plurality of struts extending in a substantially axial direction from respective proximal ends to respective distal ends thereof along respective longitudinal axes thereof,
        a belt groove which extends circumferentially about the plurality of struts, the belt groove including a distal edge that is closer to the distal ends of the struts than the proximal ends of the struts and a proximal edge that is closer to the proximal ends of the struts than the distal ends of the struts, and
        an extension extending circumferentially from a strut to a free end of the extension, the extension including a shoulder surface which extends from the strut to the free end of the extension such that the shoulder surface and a junction between the shoulder surface and the strut are disposed between the proximal edge of the belt groove and the distal edge of the belt groove;
    a belt disposed distally adjacent the shoulder surface having a first portion fixed relative to the delivery shaft and a second portion positioned circumferentially about at least a portion of the stent to retain the stent in an at least partially constrained configuration; and
    a release wire configured to releasably engage at least a portion of the belt to retain the belt;
    wherein the shoulder surface engages at least a portion of the belt to minimize axial movement of the belt during proximal retraction and release of the release wire from engagement with the belt.

8. The delivery system of claim 7 wherein the belt second portion is defined by first and second belt intermediate portions which are intertwined to define an eye loop.

9. The delivery system of claim 8 wherein the first belt intermediate portion extends tangentially relative to the delivery shaft and the second belt intermediate portion reverses upon itself to define a partial loop portion.

10. The delivery system of claim 9 wherein the shoulder surface is axially adjacent to the first belt intermediate portion.

11. The delivery system of claim 10 wherein the first intermediate portion extends from under the stent to over the release wire such that the first intermediate portion crosses the shoulder surface.

12. The delivery system of claim 8 wherein the shoulder surface is axially adjacent to the eye loop.

13. The delivery system of claim 7 wherein the stent includes a plurality struts and the shoulder extends from the strut which is the last strut which the belt second portion passes over.

14. The delivery system of claim 13 wherein the belt second portion biases the release wire toward the shoulder surface.

15. The delivery system of claim 14 wherein the release wire biases an intermediate portion of the belt toward the shoulder surface.

16. The delivery system of claim 7 wherein the free end of the extension comprises a blunted configuration.

17. A method of assembling a stent on a stent delivery shaft, the method comprising:

providing a stent including:

a plurality of struts extending in a substantially axial direction from respective proximal ends to respective distal ends thereof along respective longitudinal axes thereof, a belt groove which extends circumferentially about the plurality of struts, the belt groove including a distal edge that is closer to the distal ends of the struts than the proximal ends of the struts and a proximal edge that is closer to the proximal ends of the struts than the distal ends of the struts, and an extension extending circumferentially from a strut to a free end of the extension, the extension including a shoulder surface which extends from the strut to the free end of the extension such that the shoulder surface and a junction between the shoulder surface and the strut are disposed between the proximal edge of the belt groove and the distal edge of the belt groove;

fixing a first portion of a belt relative to the stent delivery shaft;

positioning the stent about a portion of the stent delivery shaft;

positioning a second portion of the belt circumferentially about at least a portion of the stent to retain the stent in a constrained configuration;

engaging at least a portion of the belt with a release wire to maintain the belt about the stent; and engaging at least a portion of the belt with the belt groove and the shoulder surface of the extension.

18. A stent comprising:

a plurality of substantially axially extending struts which extend from respective proximal ends to respective distal ends thereof along respective longitudinal axes thereof;

a belt groove extending circumferentially about the plurality of struts between the proximal ends and distal ends of the plurality of struts, the belt groove including a distal edge that is closer to the distal ends of the struts than the proximal ends of the struts and a proximal edge that is closer to the proximal ends of the struts than the distal ends of the struts; and an extension extending circumferentially from a strut to a free end of the extension the extension including a shoulder surface which is configured to engage a belt disposed in the belt groove during release of the belt, the shoulder surface extending from the strut to the free end of the extension such that the shoulder surface and a junction between the shoulder surface and the strut are disposed between the proximal edge of the belt groove and the distal edge of the belt groove.

19. The stent of claim 18 wherein the extension is formed integrally with the strut.

20. The stent of claim 18 wherein the extension is formed as part of a separate shoulder member that is interconnected with the strut.

21. The stent of claim 20 wherein the shoulder member is interconnected with the strut via crimping, adhesion, welding or bonding.

22. The stent of claim 18 wherein the shoulder surface is at an angle of approximately 90° relative to the longitudinal axis of the strut.

23. The stent of claim 18 wherein the free end of the extension comprises a blunted configuration.

* * * * *

UNITED STATES PATENT AND TRADEMARK OFFICE
CERTIFICATE OF CORRECTION

PATENT NO.        : 8,226,701 B2                        Page 1 of 1
APPLICATION NO.   : 11/861756
DATED             : July 24, 2012
INVENTOR(S)       : Brian A. Glynn It is certified that error appears in the above-identified patent and that said Letters Patent is hereby corrected as shown below:

In the claims
Column 8
    Claim 18, line 14 should read:
        "free end of the extension, the extension including a shoul-"

Signed and Sealed this
Third Day of November, 2015

Michelle K. Lee
*Director of the United States Patent and Trademark Office*